(12) United States Patent  
Avitable et al.

(10) Patent No.: US 8,235,923 B2
(45) Date of Patent: Aug. 7, 2012

(54) COMPRESSION DEVICE WITH REMOVABLE PORTION

(75) Inventors: Raymond Avitable, Waltham, MA (US); Arnaz Malhi, Watertown, MA (US); Rodney K. Dinkins, Easley, SC (US); Joshua Bloom, Clemson, SC (US)

(73) Assignee: Tyco Healthcare Group LP, Mansfield, MA (US)

( * ) Notice: Subject to any disclaimer, the term of this patent is extended or adjusted under 35 U.S.C. 154(b) by 947 days.

(21) Appl. No.: 12/241,914

(22) Filed: Sep. 30, 2008

(65) Prior Publication Data
US 2010/0081975 A1    Apr. 1, 2010

(51) Int. Cl.
*A61H 9/00*    (2006.01)
(52) U.S. Cl. .................................... 601/152; 601/151
(58) Field of Classification Search .......... 601/148–152; 602/13; 606/201–203; 128/DIG. 20
See application file for complete search history.

(56) References Cited

U.S. PATENT DOCUMENTS

| | | |
|---|---|---|
| 346,979 A | 8/1886 | Barr |
| 908,959 A | 1/1909 | Cooke |
| 910,689 A | 1/1909 | Kelly et al. |
| 1,510,482 A | 10/1924 | Kramer |
| 1,608,239 A | 11/1926 | Rosett |
| 2,199,408 A | 5/1940 | La Liberte |
| 2,489,388 A | 11/1949 | Rubin |
| 2,533,504 A | 12/1950 | Poor |
| 2,638,915 A | 5/1953 | Mitchell |
| 2,676,587 A | 4/1954 | Corcoran |
| 2,694,395 A | 11/1954 | Brown |
| 2,880,721 A | 4/1959 | Corcoran |
| 2,896,612 A | 7/1959 | Bates et al. |
| 2,998,817 A | 9/1961 | Armstrong |
| 3,164,152 A | 1/1965 | Vere Nicoll |
| 3,245,405 A | 4/1966 | Gardner |
| 3,288,132 A | 11/1966 | Meredith |
| 3,351,055 A | 11/1967 | Gottfried |
| 3,454,010 A | 7/1969 | Lilligren et al. |

(Continued)

FOREIGN PATENT DOCUMENTS

DE    19846922 A1    4/2000

(Continued)

OTHER PUBLICATIONS

Office action issued Nov. 18, 2010 regarding U.S. Appl. No. 12/242,268, 8 pgs.

(Continued)

*Primary Examiner* — Quang D Thanh
(74) *Attorney, Agent, or Firm* — Thomas M. Johnston, Esq.

(57) ABSTRACT

A device for applying compression treatment to a part of a wearer's body comprises first and second inflatable bladders spaced apart from one another along an axis of the device. A line of weakness in a connecting section between the first and second bladders extends generally transverse to the axis of the device for selectively separating the inflatable bladders from one another. The device includes an overlying layer in generally opposing relationship to one of the first and second bladder layers. The overlying layer is discontinuous generally adjacent to the line of weakness to define terminal edge margins of the overlying layer extending generally along the line of weakness. Each of the terminal edge margins are connected to at least one of the first and second bladder layers on an opposite side of the line of weakness from the other terminal edge margin.

22 Claims, 12 Drawing Sheets

U.S. PATENT DOCUMENTS

| | | | |
|---|---|---|---|
| 3,469,769 A | 9/1969 | Guenther | |
| 3,473,527 A | 10/1969 | Spiro | |
| 3,561,435 A | 2/1971 | Nicholson | |
| 3,568,227 A | 3/1971 | Dunham | |
| 3,606,880 A | 9/1971 | Ogle, Jr. | |
| 3,701,173 A | 10/1972 | Whitney | |
| 3,728,875 A | 4/1973 | Hartigan et al. | |
| 3,760,795 A | 9/1973 | Adelhed | |
| 3,771,519 A | 11/1973 | Haake | |
| 3,786,805 A | 1/1974 | Tourin | |
| 3,824,992 A | 7/1974 | Nicholson et al. | |
| 3,826,249 A | 7/1974 | Lee et al. | |
| 3,862,629 A | 1/1975 | Rotta | |
| 3,868,952 A | 3/1975 | Hatton | |
| 3,877,426 A | 4/1975 | Nirschl | |
| 3,878,839 A | 4/1975 | Norton et al. | |
| 3,899,210 A | 8/1975 | Samhammer et al. | |
| 3,901,221 A | 8/1975 | Nicholson et al. | |
| 3,906,937 A | 9/1975 | Aronson | |
| 3,920,006 A | 11/1975 | Lapidus | |
| D239,981 S | 5/1976 | Arbuck et al. | |
| 3,955,565 A | 5/1976 | Johnson, Jr. | |
| 4,013,069 A | 3/1977 | Hasty | |
| 4,029,087 A | 6/1977 | Dye et al. | |
| 4,030,488 A | 6/1977 | Hasty | |
| 4,054,129 A | 10/1977 | Byars et al. | |
| 4,066,084 A | 1/1978 | Tillander | |
| 4,076,022 A | 2/1978 | Walker | |
| 4,091,804 A | 5/1978 | Hasty | |
| 4,146,021 A | 3/1979 | Brosseau et al. | |
| 4,149,529 A | 4/1979 | Copeland et al. | |
| 4,149,541 A | 4/1979 | Gammons et al. | |
| 4,153,050 A | 5/1979 | Bishop et al. | |
| 4,156,425 A | 5/1979 | Arkans | |
| 4,198,961 A | 4/1980 | Arkans | |
| 4,202,312 A | 5/1980 | Mori et al. | |
| 4,202,325 A | 5/1980 | Villari et al. | |
| 4,206,751 A | 6/1980 | Schneider | |
| 4,207,875 A | 6/1980 | Arkans | |
| 4,207,876 A | 6/1980 | Annis | |
| 4,219,892 A | 9/1980 | Rigdon | |
| 4,253,449 A | 3/1981 | Arkans et al. | |
| 4,267,611 A | 5/1981 | Agulnick | |
| 4,270,527 A | 6/1981 | Peters et al. | |
| 4,280,485 A | 7/1981 | Arkans | |
| 4,294,240 A | 10/1981 | Thill | |
| 4,300,245 A | 11/1981 | Saunders | |
| 4,308,862 A | 1/1982 | Kalmar | |
| 4,311,135 A | 1/1982 | Brueckner et al. | |
| 4,320,746 A * | 3/1982 | Arkans et al. | 601/152 |
| 4,351,872 A | 9/1982 | Brosseau et al. | |
| 4,355,632 A | 10/1982 | Sandman | |
| 4,363,125 A | 12/1982 | Brewer et al. | |
| 4,372,297 A | 2/1983 | Perlin | |
| 4,375,217 A | 3/1983 | Arkans | |
| 4,379,217 A | 4/1983 | Youmans | |
| 4,402,312 A | 9/1983 | Villari et al. | |
| 4,408,599 A | 10/1983 | Mummert | |
| 4,417,587 A | 11/1983 | Ichinomiya et al. | |
| 4,437,269 A | 3/1984 | Shaw | |
| 4,442,834 A | 4/1984 | Tucker et al. | |
| 4,445,505 A | 5/1984 | Labour et al. | |
| 4,453,538 A | 6/1984 | Whitney | |
| 4,522,197 A | 6/1985 | Hasegawa | |
| 4,531,516 A | 7/1985 | Poole et al. | |
| 4,547,906 A | 10/1985 | Nishida et al. | |
| 4,547,919 A | 10/1985 | Wang | |
| 4,552,821 A | 11/1985 | Gibbard et al. | |
| 4,580,816 A | 4/1986 | Campbell et al. | |
| 4,593,692 A | 6/1986 | Flowers | |
| 4,597,384 A | 7/1986 | Whitney | |
| 4,614,179 A | 9/1986 | Gardner et al. | |
| 4,614,180 A | 9/1986 | Gardner et al. | |
| 4,624,244 A | 11/1986 | Taheri | |
| 4,624,248 A | 11/1986 | Poole et al. | |
| 4,650,452 A | 3/1987 | Jensen | |
| 4,657,003 A | 4/1987 | Wirtz | |
| 4,682,588 A | 7/1987 | Curlee | |
| 4,696,289 A | 9/1987 | Gardner et al. | |
| 4,699,424 A | 10/1987 | Andres et al. | |
| 4,702,232 A | 10/1987 | Gardner et al. | |
| 4,703,750 A | 11/1987 | Sebastian et al. | |
| 4,706,658 A | 11/1987 | Cronin | |
| 4,721,101 A | 1/1988 | Gardner et al. | |
| 4,722,332 A | 2/1988 | Saggers | |
| 4,730,606 A | 3/1988 | Leininger | |
| 4,762,121 A | 8/1988 | Shienfeld | |
| 4,773,397 A | 9/1988 | Wright et al. | |
| 4,805,620 A | 2/1989 | Meistrell | |
| 4,809,684 A | 3/1989 | Gardner et al. | |
| 4,827,912 A | 5/1989 | Carrington et al. | |
| 4,832,010 A | 5/1989 | Lerman | |
| RE32,939 E | 6/1989 | Gardner et al. | |
| RE32,940 E | 6/1989 | Gardner et al. | |
| 4,836,194 A | 6/1989 | Sebastian et al. | |
| 4,836,691 A | 6/1989 | Suzuki et al. | |
| 4,841,956 A | 6/1989 | Gardner et al. | |
| D302,301 S | 7/1989 | Robinette-Lehman | |
| 4,846,160 A | 7/1989 | Gardner et al. | |
| 4,846,189 A | 7/1989 | Sun | |
| 4,869,265 A | 9/1989 | McEwen | |
| 4,872,448 A | 10/1989 | Johnson, Jr. | |
| 4,876,788 A | 10/1989 | Steer et al. | |
| 4,883,073 A | 11/1989 | Aziz | |
| 4,886,053 A | 12/1989 | Neal | |
| 4,898,160 A | 2/1990 | Brownlee | |
| 4,938,207 A | 7/1990 | Vargo | |
| 4,938,208 A | 7/1990 | Dye | |
| 4,938,226 A | 7/1990 | Danielsson et al. | |
| 4,945,571 A | 8/1990 | Calvert | |
| 4,947,834 A | 8/1990 | Kartheus et al. | |
| 4,957,105 A | 9/1990 | Kurth | |
| 4,960,115 A | 10/1990 | Ranciato | |
| 4,964,402 A | 10/1990 | Grim et al. | |
| 4,979,953 A | 12/1990 | Spence | |
| 4,985,024 A | 1/1991 | Sipinen | |
| 4,989,273 A | 2/1991 | Cromartie | |
| 5,007,411 A | 4/1991 | Dye | |
| 5,014,681 A | 5/1991 | Neeman et al. | |
| 5,022,387 A | 6/1991 | Hasty | |
| 5,031,604 A | 7/1991 | Dye | |
| 5,048,536 A | 9/1991 | McEwen | |
| 5,052,377 A | 10/1991 | Frajdenrajch | |
| 5,062,414 A | 11/1991 | Grim | |
| 5,069,219 A | 12/1991 | Knoblich | |
| 5,080,951 A | 1/1992 | Guthrie | |
| 5,109,832 A | 5/1992 | Proctor et al. | |
| 5,117,812 A | 6/1992 | McWhorter | |
| 5,120,300 A | 6/1992 | Shaw | |
| 5,135,473 A | 8/1992 | Epler et al. | |
| 5,139,476 A | 8/1992 | Peters | |
| 5,146,932 A | 9/1992 | McCabe | |
| 5,156,629 A | 10/1992 | Shane et al. | |
| 5,158,541 A | 10/1992 | McCurley | |
| 5,168,576 A | 12/1992 | Krent et al. | |
| 5,172,689 A | 12/1992 | Wright | |
| D332,495 S | 1/1993 | Lake | |
| 5,179,941 A | 1/1993 | Siemssen et al. | |
| 5,181,522 A | 1/1993 | McEwen | |
| 5,186,163 A | 2/1993 | Dye | |
| 5,193,549 A | 3/1993 | Bellin et al. | |
| 5,211,162 A | 5/1993 | Gillen, Jr. et al. | |
| 5,226,245 A | 7/1993 | Lamont | |
| 5,226,564 A | 7/1993 | Steer et al. | |
| 5,230,335 A | 7/1993 | Johnson, Jr. et al. | |
| 5,245,990 A | 9/1993 | Bertinin | |
| 5,259,397 A | 11/1993 | McCabe | |
| 5,263,473 A | 11/1993 | McWhorter | |
| 5,277,695 A | 1/1994 | Johnson, Jr. et al. | |
| 5,277,697 A | 1/1994 | France et al. | |
| 5,288,286 A | 2/1994 | Davis et al. | |
| 5,314,455 A | 5/1994 | Johnson, Jr. et al. | |
| 5,334,135 A | 8/1994 | Grim et al. | |
| 5,342,285 A | 8/1994 | Dye | |
| 5,354,260 A | 10/1994 | Cook | |
| 5,378,224 A | 1/1995 | Billotti | |
| 5,383,894 A | 1/1995 | Dye | |

| | | | | | | |
|---|---|---|---|---|---|---|
| 5,383,919 | A | 1/1995 | Kelly et al. | 5,830,164 A | 11/1998 | Cone et al. |
| 5,385,538 | A | 1/1995 | Mann | 5,833,639 A | 11/1998 | Nunes et al. |
| 5,389,065 | A | 2/1995 | Johnson, Jr. | 5,840,049 A | 11/1998 | Tumey et al. |
| 5,391,141 | A | 2/1995 | Hamilton | 5,843,007 A | 12/1998 | McEwen et al. |
| 5,399,153 | A | 3/1995 | Caprio, Jr. et al. | D403,775 S | 1/1999 | Davis et al. |
| 5,403,265 | A | 4/1995 | Berguer et al. | D405,884 S | 2/1999 | Roper |
| 5,407,421 | A | 4/1995 | Goldsmith | 5,876,359 A | 3/1999 | Bock et al. |
| D358,216 | S | 5/1995 | Dye | 5,891,065 A | 4/1999 | Cariapa et al. |
| 5,413,142 | A | 5/1995 | Johnson et al. | 5,894,682 A | 4/1999 | Broz |
| 5,413,582 | A | 5/1995 | Eaton | D411,301 S | 6/1999 | Hampson et al. |
| 5,414,081 | A | 5/1995 | Horikawa et al. | 5,916,183 A | 6/1999 | Reid |
| 5,419,757 | A | 5/1995 | Daneshvar | 5,925,010 A | 7/1999 | Caprio, Jr. |
| 5,425,701 | A | 6/1995 | Oster et al. | 5,926,850 A | 7/1999 | Han |
| 5,435,009 | A | 7/1995 | Schild et al. | 5,931,797 A | 8/1999 | Tumey et al. |
| 5,437,595 | A | 8/1995 | Smith | 5,938,628 A | 8/1999 | Oguri et al. |
| 5,437,610 | A | 8/1995 | Cariapa et al. | 5,951,502 A | 9/1999 | Peeler et al. |
| 5,441,533 | A | 8/1995 | Johnson et al. | 5,957,872 A | 9/1999 | Flick |
| 5,443,440 | A | 8/1995 | Tumey et al. | 5,966,763 A | 10/1999 | Thomas et al. |
| 5,449,341 | A | 9/1995 | Harris | 5,968,072 A | 10/1999 | Hite et al. |
| 5,449,379 | A | 9/1995 | Hadtke | 5,976,099 A | 11/1999 | Kellogg |
| 5,450,858 | A | 9/1995 | Zablotsky et al. | 5,976,300 A | 11/1999 | Buchanan et al. |
| 5,451,201 | A | 9/1995 | Prengler | 5,988,704 A | 11/1999 | Ryhman |
| 5,453,081 | A | 9/1995 | Hansen | 5,989,204 A | 11/1999 | Lina |
| 5,458,265 | A | 10/1995 | Hester et al. | 5,991,654 A | 11/1999 | Tumey et al. |
| 5,462,517 | A | 10/1995 | Mann | 5,997,495 A | 12/1999 | Cook et al. |
| 5,466,250 | A | 11/1995 | Johnson, Jr. et al. | 5,997,981 A | 12/1999 | McCormack et al. |
| 5,470,156 | A | 11/1995 | May | 6,001,119 A | 12/1999 | Hampson et al. |
| 5,478,119 | A | 12/1995 | Dye | 6,007,559 A | 12/1999 | Arkans |
| 5,489,252 | A | 2/1996 | May | 6,010,471 A | 1/2000 | Ben-Noon |
| 5,489,259 | A | 2/1996 | Jacobs et al. | 6,021,780 A | 2/2000 | Darby |
| 5,496,262 | A | 3/1996 | Johnson, Jr. et al. | 6,036,718 A | 3/2000 | Ledford et al. |
| 5,503,620 | A | 4/1996 | Danzger | 6,048,326 A | 4/2000 | Davis et al. |
| 5,511,552 | A | 4/1996 | Johnson | 6,051,016 A | 4/2000 | Mesaros et al. |
| 5,513,658 | A | 5/1996 | Goseki | 6,062,244 A | 5/2000 | Arkans |
| 5,514,155 | A | 5/1996 | Daneshvar | 6,066,217 A | 5/2000 | Dibble et al. |
| 5,527,267 | A | 6/1996 | Billotti | 6,076,193 A | 6/2000 | Hood |
| 5,554,105 | A | 9/1996 | Taylor | 6,080,120 A | 6/2000 | Sandman et al. |
| D376,013 | S | 11/1996 | Sandman et al. | D428,153 S | 7/2000 | Davis |
| 5,575,762 | A | 11/1996 | Peeler et al. | 6,110,135 A | 8/2000 | Madow et al. |
| 5,578,055 | A | 11/1996 | McEwen | 6,126,683 A | 10/2000 | Momtaheni |
| 5,584,798 | A | 12/1996 | Fox | 6,129,688 A | 10/2000 | Arkans |
| 5,588,954 | A | 12/1996 | Ribando et al. | 6,129,695 A | 10/2000 | Peters et al. |
| 5,588,955 | A | 12/1996 | Johnson, Jr. et al. | 6,135,116 A | 10/2000 | Vogel et al. |
| 5,588,956 | A | 12/1996 | Billotti | 6,145,143 A | 11/2000 | Hicks et al. |
| 5,591,200 | A | 1/1997 | Cone et al. | 6,149,600 A | 11/2000 | Poorman-Ketchum |
| 5,591,337 | A | 1/1997 | Lynn et al. | 6,152,495 A | 11/2000 | Hoffmann et al. |
| 5,603,690 | A | 2/1997 | Barry | 6,152,893 A | 11/2000 | Pigg et al. |
| 5,609,570 | A | 3/1997 | Lamont | 6,168,539 B1 | 1/2001 | Maina |
| 5,620,411 | A | 4/1997 | Schumann et al. | 6,171,271 B1 | 1/2001 | Hörnberg |
| 5,626,556 | A | 5/1997 | Tobler et al. | 6,179,796 B1 | 1/2001 | Waldridge |
| 5,626,557 | A | 5/1997 | Mann | 6,197,045 B1 | 3/2001 | Carson |
| 5,634,889 | A | 6/1997 | Gardner et al. | 6,203,510 B1 * | 3/2001 | Takeuchi et al. .............. 601/152 |
| 5,637,106 | A | 6/1997 | Mitchell et al. | 6,209,159 B1 | 4/2001 | Murphy |
| 5,640,714 | A | 6/1997 | Tanaka | 6,212,719 B1 | 4/2001 | Thomas et al. |
| 5,649,954 | A | 7/1997 | McEwen | 6,231,507 B1 | 5/2001 | Zikorus et al. |
| 5,653,244 | A | 8/1997 | Shaw | 6,231,532 B1 | 5/2001 | Watson et al. |
| D383,547 | S | 9/1997 | Mason et al. | 6,245,023 B1 | 6/2001 | Clemmons |
| 5,664,270 | A | 9/1997 | Bell et al. | 6,254,554 B1 | 7/2001 | Turtzo |
| 5,669,872 | A | 9/1997 | Fox | 6,257,626 B1 | 7/2001 | Campau |
| 5,674,262 | A | 10/1997 | Tumey | 6,257,627 B1 | 7/2001 | Fujiwara et al. |
| 5,678,558 | A | 10/1997 | Johnson | 6,273,866 B2 | 8/2001 | Thomas et al. |
| 5,695,453 | A | 12/1997 | Neal | 6,290,662 B1 | 9/2001 | Morris et al. |
| 5,704,999 | A | 1/1998 | Lukich et al. | 6,290,664 B1 | 9/2001 | Nauert |
| 5,711,757 | A | 1/1998 | Bryant | 6,296,617 B1 | 10/2001 | Peeler et al. |
| 5,717,996 | A | 2/1998 | Feldmann | 6,315,745 B1 | 11/2001 | Kloecker |
| 5,720,739 | A | 2/1998 | Hilston et al. | 6,319,215 B1 | 11/2001 | Manor et al. |
| 5,725,485 | A | 3/1998 | Ribando et al. | 6,322,530 B1 | 11/2001 | Johnson, Jr. et al. |
| 5,728,055 | A | 3/1998 | Sebastian | 6,336,935 B1 | 1/2002 | Davis et al. |
| 5,728,057 | A | 3/1998 | Ouellette et al. | 6,338,723 B1 | 1/2002 | Carpenter et al. |
| 5,730,710 | A | 3/1998 | Eichhorn et al. | 6,349,506 B1 | 2/2002 | Pace et al. |
| 5,741,295 | A | 4/1998 | McEwen | 6,358,219 B1 | 3/2002 | Arkans |
| 5,746,213 | A | 5/1998 | Marks | 6,361,496 B1 | 3/2002 | Zikorus et al. |
| 5,769,800 | A | 6/1998 | Gelfand et al. | 6,368,357 B1 | 4/2002 | Schon et al. |
| 5,769,801 | A | 6/1998 | Tumey et al. | 6,375,633 B1 | 4/2002 | Endress et al. |
| 5,772,880 | A | 6/1998 | Lynn et al. | 6,385,778 B1 | 5/2002 | Johnson |
| 5,790,998 | A | 8/1998 | Crescimbeni | 6,385,864 B1 | 5/2002 | Sell, Jr. et al. |
| 5,795,312 | A | 8/1998 | Dye | 6,387,065 B1 | 5/2002 | Tumey |
| 5,797,851 | A | 8/1998 | Byrd | 6,402,879 B1 | 6/2002 | Tawney et al. |
| 5,823,981 | A | 10/1998 | Grim et al. | 6,409,691 B1 | 6/2002 | Dakin et al. |

| | | |
|---|---|---|
| 6,421,859 B1 | 7/2002 | Hicks et al. |
| 6,423,053 B1 | 7/2002 | Lee |
| 6,436,064 B1 | 8/2002 | Kloecker |
| 6,440,093 B1 | 8/2002 | McEwen et al. |
| 6,447,460 B1 | 9/2002 | Zheng et al. |
| 6,447,467 B1 | 9/2002 | Barak |
| 6,463,934 B1 | 10/2002 | Johnson, Jr. et al. |
| 6,468,237 B1 | 10/2002 | Lina |
| 6,478,757 B1 | 11/2002 | Barak |
| 6,488,643 B1 | 12/2002 | Tumey et al. |
| 6,493,568 B1 | 12/2002 | Bell et al. |
| 6,494,852 B1 | 12/2002 | Barak et al. |
| 6,508,205 B1 | 1/2003 | Zink |
| 6,520,926 B2 | 2/2003 | Hall |
| 6,526,597 B1 | 3/2003 | Shepard |
| 6,527,727 B2 | 3/2003 | Itonaga et al. |
| 6,537,298 B2 | 3/2003 | Dedo |
| 6,540,707 B1 | 4/2003 | Stark et al. |
| 6,544,202 B2 | 4/2003 | McEwen et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph |
| 6,558,338 B1 | 5/2003 | Wasserman |
| 6,589,267 B1 | 7/2003 | Hui |
| 6,589,534 B1 | 7/2003 | Shaul et al. |
| 6,592,534 B1 | 7/2003 | Rutt et al. |
| 6,593,508 B1 | 7/2003 | Harder |
| 6,598,249 B2 | 7/2003 | Pajanacci et al. |
| D478,995 S | 8/2003 | Cipra et al. |
| 6,616,622 B1 | 9/2003 | Barberio |
| 6,618,859 B1 | 9/2003 | Kadymir et al. |
| 6,629,941 B1 | 10/2003 | Ishibashi et al. |
| 6,645,165 B2 | 11/2003 | Waldridge et al. |
| D484,986 S | 1/2004 | Cipra et al. |
| 6,682,547 B2 | 1/2004 | McEwen et al. |
| 6,685,661 B2 | 2/2004 | Peled |
| 6,719,711 B1 | 4/2004 | Islava |
| 6,726,641 B2 | 4/2004 | Chiang et al. |
| 6,746,470 B2 | 6/2004 | McEwen et al. |
| 6,757,516 B2 | 6/2004 | Miura |
| 6,762,337 B2 | 7/2004 | Boukanov et al. |
| 6,762,338 B2 | 7/2004 | Harder |
| 6,842,915 B2 | 1/2005 | Turner et al. |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| D506,553 S | 6/2005 | Tesluk |
| 6,945,944 B2 | 9/2005 | Kuiper et al. |
| D510,626 S | 10/2005 | Krahner et al. |
| 6,966,884 B2 | 11/2005 | Waldridge et al. |
| 6,984,215 B2 | 1/2006 | Shah |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| 7,063,676 B2 | 6/2006 | Barak et al. |
| 7,104,967 B2 | 9/2006 | Rothman et al. |
| D533,668 S | 12/2006 | Brown |
| 7,166,077 B2 | 1/2007 | Millay et al. |
| 7,214,202 B1 | 5/2007 | Vogel et al. |
| 7,217,249 B2 | 5/2007 | Scott |
| D545,972 S | 7/2007 | Wieringa et al. |
| 7,237,272 B2 | 7/2007 | Botcher |
| 7,238,080 B2 | 7/2007 | Gimble |
| 7,244,483 B2 | 7/2007 | Tawney et al. |
| 7,258,676 B2 | 8/2007 | Calderon et al. |
| D550,367 S | 9/2007 | Nash |
| 7,276,037 B2 | 10/2007 | Ravikumar |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,285,103 B2 | 10/2007 | Nathanson |
| 7,288,076 B2 | 10/2007 | Grim et al. |
| 7,297,128 B2 | 11/2007 | Binder et al. |
| 7,303,539 B2 | 12/2007 | Binder et al. |
| 7,306,568 B2 | 12/2007 | Diana |
| 7,310,847 B2 | 12/2007 | Bolkan et al. |
| 7,318,812 B2 | 1/2008 | Taylor et al. |
| D562,461 S | 2/2008 | Nash |
| D562,462 S | 2/2008 | Muir et al. |
| 7,326,227 B2 | 2/2008 | Dedo et al. |
| 7,329,232 B2 | 2/2008 | Lipshaw et al. |
| 7,351,217 B2 | 4/2008 | Scherpenborg |
| 7,353,770 B2 | 4/2008 | Sanguinetti |
| 7,354,410 B2 | 4/2008 | Perry et al. |
| 7,354,411 B2 | 4/2008 | Perry et al. |
| 7,374,550 B2 | 5/2008 | Hansen et al. |
| D577,124 S | 9/2008 | Freeland et al. |
| 7,424,936 B2 | 9/2008 | McClellan |
| 7,465,283 B2 | 12/2008 | Grim et al. |
| 7,468,048 B2 | 12/2008 | Meehan |
| 7,473,816 B2 | 1/2009 | Hall |
| D594,561 S | 6/2009 | Freeland et al. |
| 7,543,399 B2 | 6/2009 | Kilgore et al. |
| 7,559,908 B2 | 7/2009 | Ravikumar |
| 7,578,799 B2 | 8/2009 | Thorsteinsson et al. |
| 7,591,796 B1 | 9/2009 | Barak et al. |
| 7,591,797 B2 | 9/2009 | Hakonson et al. |
| 7,597,675 B2 | 10/2009 | Ingimundarson et al. |
| 7,615,027 B2 | 11/2009 | Nordt, III et al. |
| 7,618,389 B2 | 11/2009 | Nordt, III et al. |
| 7,625,348 B2 | 12/2009 | Young et al. |
| 7,637,879 B2 | 12/2009 | Barak et al. |
| D608,006 S | 1/2010 | Avitable et al. |
| 7,654,117 B2 | 2/2010 | Barnett |
| 7,748,090 B2 | 7/2010 | Seth et al. |
| 2001/0018564 A1 | 8/2001 | Manor et al. |
| 2002/0068886 A1 | 6/2002 | Lin |
| 2002/0069731 A1 | 6/2002 | Soucy |
| 2002/0115949 A1 | 8/2002 | Kuslich et al. |
| 2003/0018313 A1 | 1/2003 | Tanzer et al. |
| 2003/0083605 A1 | 5/2003 | Edmund |
| 2003/0139255 A1 | 7/2003 | Lina |
| 2003/0199922 A1 | 10/2003 | Buckman |
| 2004/0010212 A1 | 1/2004 | Kuiper et al. |
| 2004/0039317 A1 | 2/2004 | Souney et al. |
| 2004/0039413 A1 | 2/2004 | Akerfeldt et al. |
| 2004/0054306 A1 | 3/2004 | Roth et al. |
| 2004/0068290 A1 | 4/2004 | Bates et al. |
| 2004/0097860 A1 | 5/2004 | Tauber |
| 2004/0158283 A1 | 8/2004 | Shook et al. |
| 2004/0158285 A1 | 8/2004 | Pillai |
| 2004/0176715 A1 | 9/2004 | Nelson |
| 2004/0181156 A1 | 9/2004 | Kingsford et al. |
| 2004/0181254 A1 | 9/2004 | Choi et al. |
| 2004/0199090 A1 | 10/2004 | Sanders et al. |
| 2004/0210167 A1 | 10/2004 | Webster |
| 2004/0236258 A1 | 11/2004 | Burns et al. |
| 2005/0070828 A1 | 3/2005 | Hampson et al. |
| 2005/0143683 A1 | 6/2005 | Waldridge et al. |
| 2005/0154336 A1 | 7/2005 | Kloecker et al. |
| 2005/0187501 A1 | 8/2005 | Ravikumar |
| 2005/0187503 A1* | 8/2005 | Tordella et al. ................ 602/13 |
| 2005/0209545 A1 | 9/2005 | Farrow et al. |
| 2005/0242315 A1 | 11/2005 | Lund |
| 2005/0261617 A1 | 11/2005 | Hall |
| 2006/0010574 A1 | 1/2006 | Linnane et al. |
| 2006/0020236 A1 | 1/2006 | Ben-Nun |
| 2006/0135894 A1 | 6/2006 | Linnane et al. |
| 2006/0142719 A1 | 6/2006 | Vogt et al. |
| 2006/0161081 A1 | 7/2006 | Barak et al. |
| 2006/0189907 A1 | 8/2006 | Pick et al. |
| 2006/0211965 A1 | 9/2006 | Horn et al. |
| 2007/0038167 A1 | 2/2007 | Tabron et al. |
| 2007/0088239 A1 | 4/2007 | Roth et al. |
| 2007/0129658 A1 | 6/2007 | Hampson et al. |
| 2007/0135742 A1 | 6/2007 | Meyer et al. |
| 2007/0135743 A1 | 6/2007 | Meyer |
| 2007/0135835 A1 | 6/2007 | McEwen et al. |
| 2007/0135836 A1 | 6/2007 | McEwen et al. |

| | | |
|---|---|---|
| 2007/0161933 A1 | 7/2007 | Ravikumar |
| 2007/0167892 A1 | 7/2007 | Gramza et al. |
| 2007/0167895 A1 | 7/2007 | Gramza et al. |
| 2007/0179416 A1 | 8/2007 | Obrien et al. |
| 2007/0197943 A1 | 8/2007 | Hakonson et al. |
| 2007/0197944 A1 | 8/2007 | Bruce et al. |
| 2007/0197947 A1 | 8/2007 | Scott |
| 2007/0219580 A1 | 9/2007 | McEwen et al. |
| 2007/0244506 A1 | 10/2007 | McEwen et al. |
| 2007/0260162 A1 | 11/2007 | Meyer et al. |
| 2007/0261789 A1 | 11/2007 | Giori |
| 2007/0276310 A1 | 11/2007 | Lipshaw et al. |
| 2007/0276311 A1 | 11/2007 | Wieringa et al. |
| 2007/0282233 A1 | 12/2007 | Meyer et al. |
| 2008/0000477 A1 | 1/2008 | Huster et al. |
| 2008/0004555 A1 | 1/2008 | Reis et al. |
| 2008/0004560 A1 | 1/2008 | Miskie |
| 2008/0021363 A1 | 1/2008 | Fee |
| 2008/0023423 A1 | 1/2008 | Duffy |
| 2008/0034479 A1 | 2/2008 | Barnett |
| 2008/0039756 A1 | 2/2008 | Thorsteinsson et al. |
| 2008/0039757 A1 | 2/2008 | Nordt, III et al. |
| 2008/0064996 A1 | 3/2008 | Bretl et al. |
| 2008/0071204 A1 | 3/2008 | Linnane et al. |
| 2008/0072629 A1 | 3/2008 | Gehring |
| 2008/0086071 A1 | 4/2008 | Weatherly |
| 2008/0103397 A1 | 5/2008 | Barak |
| 2008/0103422 A1 | 5/2008 | Perry et al. |
| 2008/0119771 A1 | 5/2008 | Jaccard |
| 2008/0188786 A1 | 8/2008 | Hickling |
| 2008/0208092 A1 | 8/2008 | Sawa |
| 2008/0234615 A1 | 9/2008 | Cook et al. |
| 2008/0243173 A1 | 10/2008 | Thorpe |
| 2008/0245361 A1 | 10/2008 | Brown |
| 2008/0249440 A1 | 10/2008 | Avitable et al. |
| 2008/0249441 A1 | 10/2008 | Avitable et al. |
| 2008/0249442 A1 | 10/2008 | Brown et al. |
| 2008/0249443 A1 | 10/2008 | Avitable et al. |
| 2008/0249444 A1 | 10/2008 | Avitable et al. |
| 2008/0249447 A1 | 10/2008 | Brown et al. |
| 2008/0249449 A1 | 10/2008 | Brown et al. |
| 2008/0249455 A1 | 10/2008 | Brown et al. |
| 2008/0249559 A1 | 10/2008 | Brown et al. |
| 2008/0250551 A1 | 10/2008 | Mazzarolo |
| 2008/0255485 A1 | 10/2008 | Johnson et al. |
| 2008/0281351 A1 | 11/2008 | Croushorn et al. |
| 2008/0306420 A1 | 12/2008 | Vess |
| 2008/0312682 A1 | 12/2008 | Shams et al. |
| 2009/0005718 A1 | 1/2009 | Lightbourne |
| 2009/0062703 A1 | 3/2009 | Meyer et al. |
| 2009/0064919 A1 | 3/2009 | Greenwald |
| 2009/0076432 A1 | 3/2009 | Winkler |
| 2009/0082708 A1 | 3/2009 | Scott et al. |
| 2009/0099562 A1 | 4/2009 | Ingimudarson et al. |
| 2009/0110890 A1 | 4/2009 | Garza et al. |
| 2009/0124944 A1 | 5/2009 | Ravikumar |
| 2009/0133446 A1 | 5/2009 | Burrow et al. |
| 2009/0137938 A1 | 5/2009 | Parivash |
| 2009/0163842 A1 | 6/2009 | Cropper |
| 2009/0171223 A1 | 7/2009 | McEwen et al. |
| 2009/0177222 A1 | 7/2009 | Brown et al. |
| 2009/0198261 A1 | 8/2009 | Schweikert |
| 2009/0227917 A1 | 9/2009 | Nardi |
| 2009/0227919 A1 | 9/2009 | Nardi et al. |
| 2009/0227922 A1 | 9/2009 | Nardi et al. |
| 2009/0234265 A1 | 9/2009 | Reid et al. |
| 2009/0278707 A1 | 11/2009 | Biggins et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0004676 A1 | 1/2010 | McEwen et al. |
| 2010/0016771 A1 | 1/2010 | Arbesman et al. |
| 2010/0022930 A1 | 1/2010 | Koby et al. |
| 2010/0042026 A1 | 2/2010 | Kloecker et al. |
| 2010/0042028 A1 | 2/2010 | Frank et al. |
| 2010/0082060 A1 | 4/2010 | Avitable |

FOREIGN PATENT DOCUMENTS

| | | |
|---|---|---|
| EP | 0221636 A1 | 5/1987 |
| EP | 0303029 A1 | 2/1989 |
| EP | 0408049 A2 | 1/1991 |
| EP | 0861651 A1 | 9/1998 |
| EP | 0893115 A2 | 1/1999 |
| EP | 1468816 A1 | 10/2004 |
| FR | 2813770 A1 | 3/2002 |
| GB | 2061086 A | 5/1981 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 2002065782 | 3/2002 |
| JP | 2004081709 | 3/2004 |
| JP | 2005066247 | 3/2005 |
| WO | 96/20685 A1 | 7/1996 |
| WO | 2004021950 A1 | 3/2004 |
| WO | 2005082315 A1 | 9/2005 |
| WO | 2006039242 A2 | 4/2006 |
| WO | 2006083865 A2 | 8/2006 |

OTHER PUBLICATIONS

Response filed Dec. 13, 2010 to Office Action dated Nov. 18, 2010 regarding U.S. Appl. No. 12/242,268, 5 pgs.

Office action issued Jan. 20, 2011 regarding U.S. Appl. No. 12/242,268, 14 pgs.

Response filed Apr. 19, 2011 to Office Action dated Jan. 20, 2011 regarding U.S. Appl. No. 12/242,268, 13 pgs.

Office action issued May 24, 2011 regarding U.S. Appl. No. 12/242,268, 15 pgs.

Mittelman, Jonathan S., MD: "Effectiveness of Leg Compression in Preventing Venous Stasis", The American Journal of Surgery, Dec 1982, p. 611-613, vol. 144, No. 6, Elsevier Publ., Bridgewater, NJ, USA.

Tyco Healthcare Kendall, SCD Response Catalog, Mar. 2000, pp. 1-2.

Tyco Healthcare Kendall, SCD Soft Sleeve Catalog, Apr. 2001, pp. 1-2.

The Kendall Company, Vascular Therapy Products Catalog, Jan. 1996, pp. 8-5 thru 8-7.

The Kendall Company, The New SCD Compression Sleeve, Aug. 1993, pp. 1-2.

Tyco Healthcare Kendall, Prevention Gets Personal Mar. 2001, pp. 1, 2, 4.

Kendall SCD, Sequential Compression Sleeves, Patent Information, Jan. 1993, 6 pages.

European Search Report regarding related application serial No. EP 09170465.0 dated Feb. 4, 2010, 6 pgs.

* cited by examiner

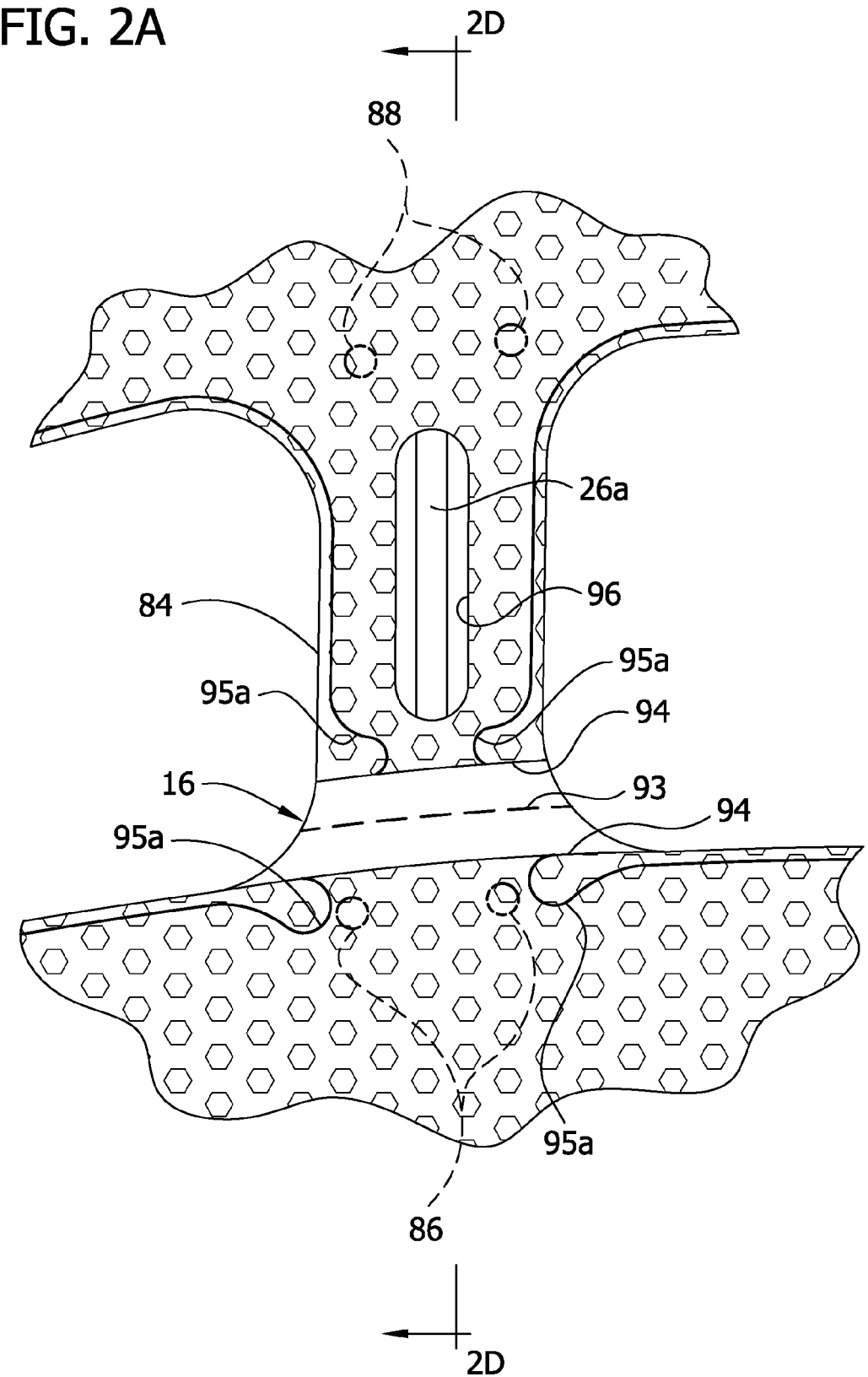

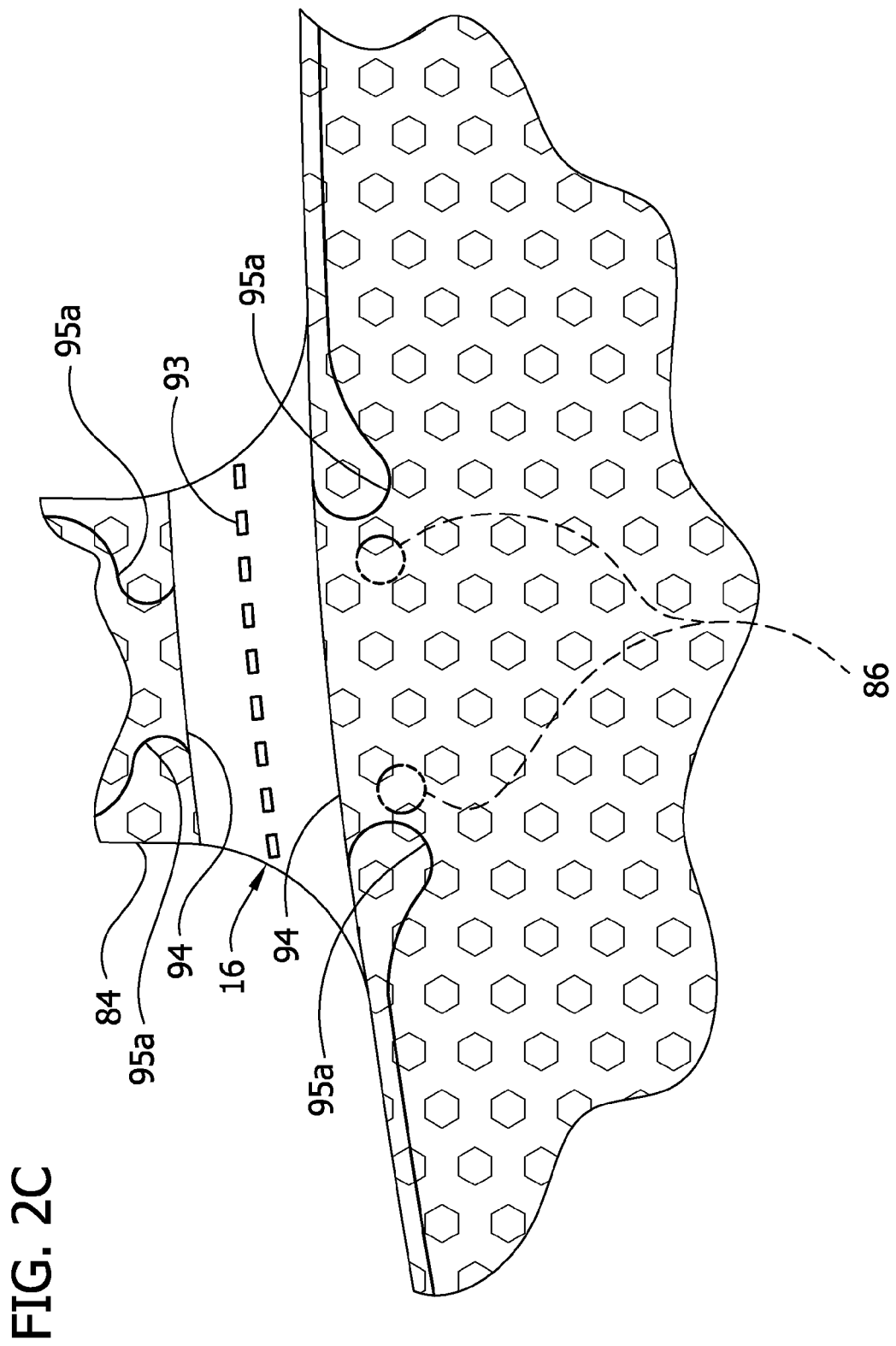

_

COMPRESSION DEVICE WITH REMOVABLE PORTION

CROSS-REFERENCE TO RELATED APPLICATIONS

This application is related to co-assigned U.S. application Ser. Nos. 11/733,095; 11/733,074; 11/733,084; 11/733,088; 11/733,077; 11/733,082; 11/733,087; 11/733,101, each of which was filed on Apr. 9, 2007, and Ser. No. 12/098,884, filed on Apr. 7, 2008, the disclosures of which are incorporated herein by reference.

FIELD OF THE INVENTION

The present invention is directed generally to a compression device for applying compression therapy to a body part of a wearer, more particularly a compression device with a removable portion.

BACKGROUND OF THE INVENTION

A major concern for immobile patients and persons alike are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated to the heart. For example, when blood circulation in these veins is retarded due to illness, injury or inactivity, there is a tendency for blood to accumulate or pool. A static pool of blood is ideal for clot formations. A major risk associated with this condition is interference with cardiovascular circulation. Most seriously, a fragment of the blood clot can break loose and migrate. A pulmonary emboli can form blocking a main pulmonary artery, which may be life threatening.

The conditions and resulting risks associated with patient immobility may be controlled or alleviated by applying intermittent pressure to a patient's limb, such as, for example, a leg to assist in blood circulation. Known devices have been employed to assist in blood circulation, such as, one piece pads and compression boots. See, for example, U.S. Pat. Nos. 6,290,662 and 6,494,852.

For example, sequential compression devices have been used, which consist of an air pump connected to a disposable wraparound pad by a series of air tubes. The wraparound pad is placed around the patient's leg. Air is then forced into different parts of the wraparound pad in sequence, creating pressure around the calves and improving venous return.

These known devices may suffer from various drawbacks due to their bulk and cumbersome nature of use. These drawbacks reduce comfort, compliance and may disadvantageously prevent mobility of the patient as recovery progresses after surgery.

Therefore, it would be desirable to overcome the disadvantages and drawbacks of the prior art with a prophylaxis sequential compression device that reduces bulk and is not cumbersome during use to improve comfort and compliance to a patient. It would be desirable if the prophylaxis sequential compression device includes a removable portion to achieve the advantages of the present disclosure. A compression sleeve having a removable thigh section is disclosed in co-assigned U.S. patent application Ser. No. 10/784,607, filed Feb. 24, 2004, and the disclosure of this application is incorporated herein by reference. The thigh section can be removed by tearing the compression sleeve along a perforation provided in the bladder material. However, this application does not address issues associated with tearing to multiple layers of differing composition to disconnect a section of the compression device.

SUMMARY OF THE INVENTION

In one aspect, a device for applying compression treatment to a part of a wearer's body generally comprises first and second opposing bladder layers secured to one another along two bladder lines to define first and second inflatable bladders spaced apart from one another along an axis of the device. A connecting section including a portion of at least one of the first and second bladder layers extends between and connecting the first and second inflatable bladders to one another. A line of weakness in the connecting section extends generally transverse to the axis of the device for selectively separating the inflatable bladders from one another. An overlying layer is in generally opposing relationship to one of the first and second bladder layers. The overlying layer is discontinuous generally adjacent to the line of weakness to define terminal edge margins of the overlying layer extending generally along the line of weakness. The terminal edge margins each are connected to at least one of the first and second bladder layers on an opposite side of the line of weakness from the other terminal edge margin.

In another aspect, a method of making a compression device generally comprises securing first and second opposing bladder layers to one another along two bladder lines to define first and second inflatable bladders spaced apart from one another along an axis of the device and having a connecting section extending between and connecting the first and second inflatable bladders to one another. A line of weakness is formed in the connecting section extending generally transverse to the axis of the device for selectively separating the inflatable bladders from one another. An overlying layer is secured in generally opposing relationship to one of the first and second bladder layers. The overlying layer is discontinuous generally adjacent to the line of weakness to define opposing terminal edge margins. Each of the terminal edge margins is secured to one of the first and second bladder layers on a respective opposite side of the line of weakness.

Other features will be in part apparent and in part pointed out hereinafter.

BRIEF DESCRIPTION OF THE DRAWINGS

FIG. 2A is an enlarged, fragmentary view of FIG. 1 showing a perforation line extending across a left bridge of the compression sleeve;

FIG. 2C is similar to FIG. 2A with the perforation line comprising slot-shaped openings;

Corresponding reference characters indicate corresponding parts throughout the drawings.

DETAILED DESCRIPTION OF THE DRAWINGS

Figure 1:
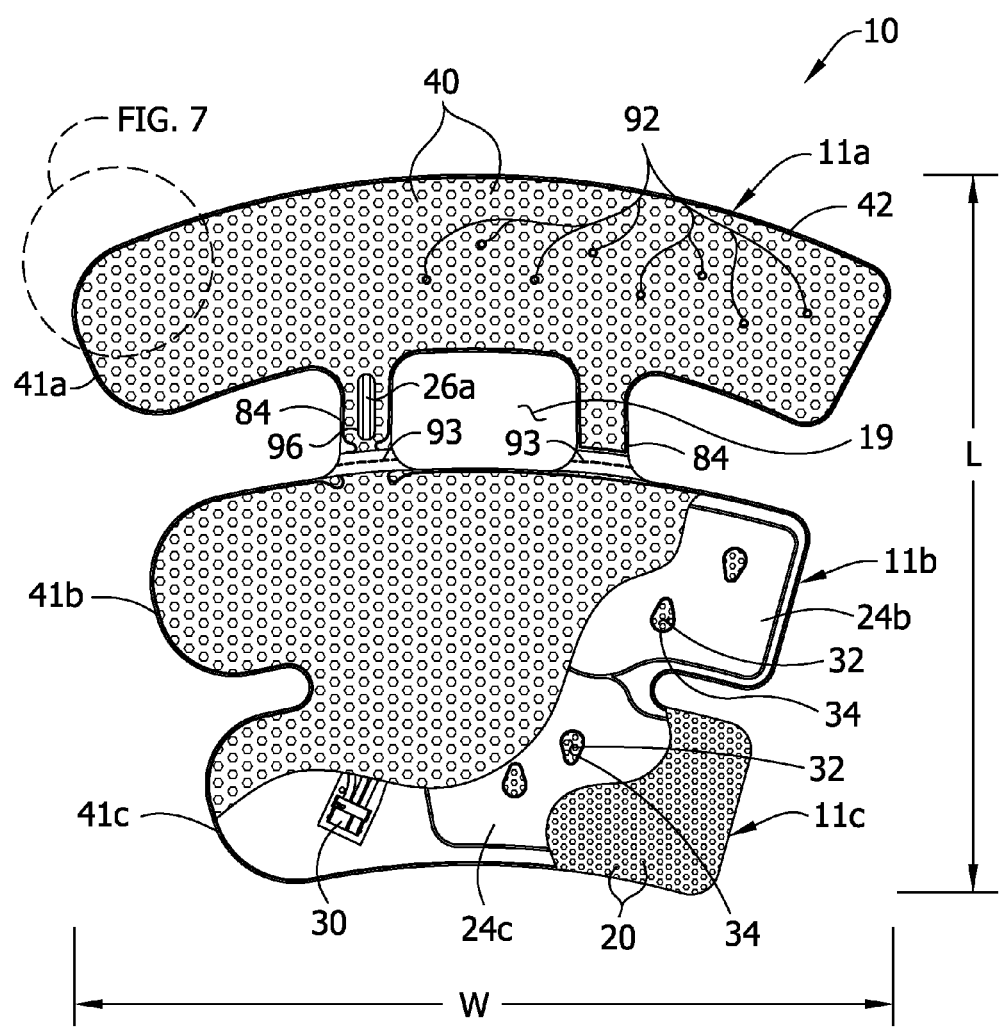
FIG. 1 is a front elevation of one embodiment of a compression sleeve with an outer cover and bladder layers of the sleeve partially removed to show underlying layers.
Figure 2:
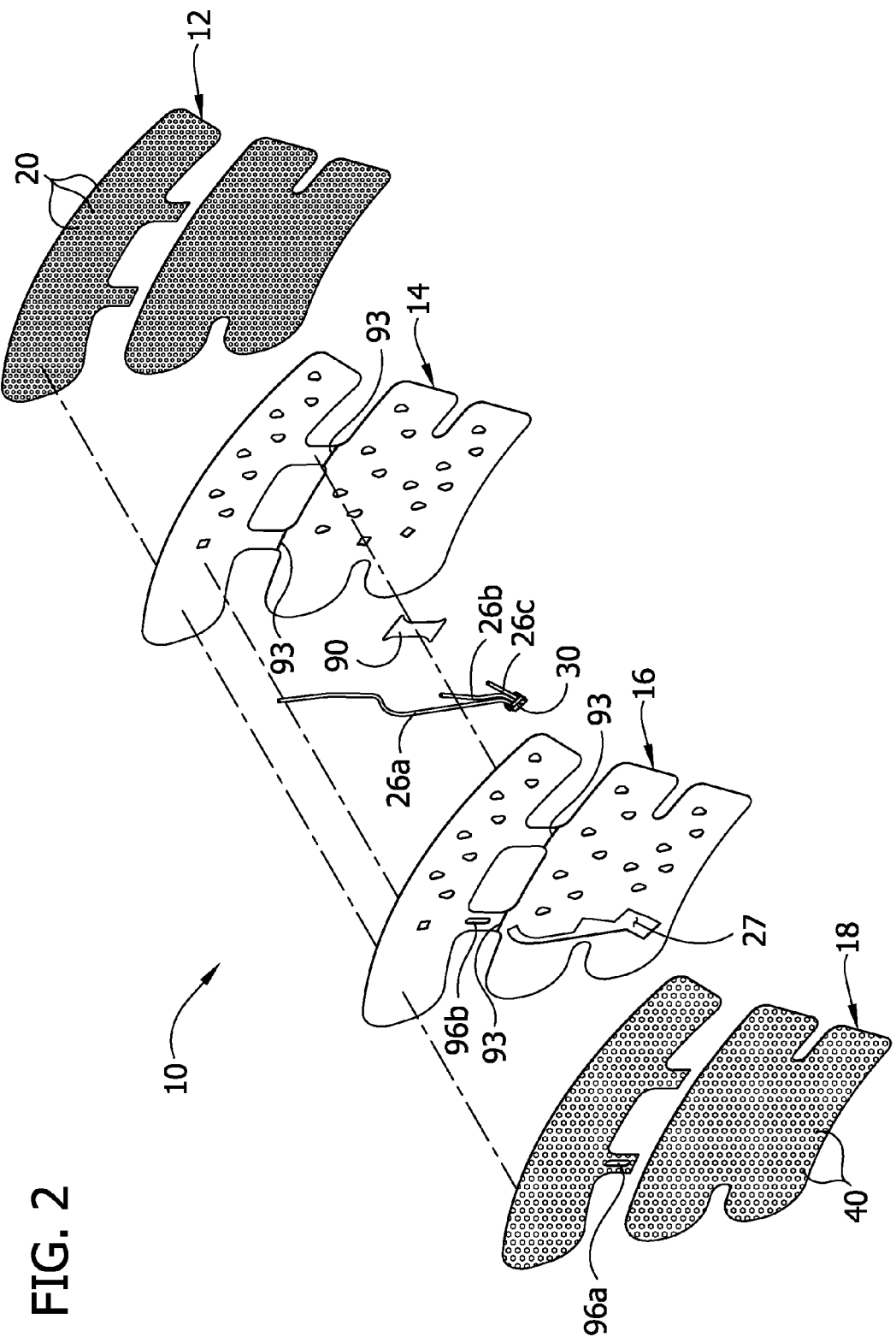
FIG. 2 is an exploded perspective of the compression sleeve.

Referring now to the drawings, and in particular to FIGS. 1 and 2, one embodiment of a compression device (broadly, "a garment or a sleeve") is generally indicated at 10 for applying sequential compression therapy to a limb of a wearer. The compression sleeve is of the type sized and shaped for being disposed around a leg of the wearer, but could be configured for application to other parts of the wearer's body. More specifically, the sleeve 10 has a width W (FIG. 1) for being wrapped around a full circumference of the leg and a length L (FIG. 1) for running from the ankle to a thigh of the leg. This type of sleeve is generally referred to in the art as a thigh-length sleeve including a thigh section 11a, a calf section 11b and an ankle section 11c. It will be understood that a compression sleeve may come in different sizes, such as a knee length sleeve (FIG. 20) that extends from the ankle up the calf of the leg. It is understood that other types of compression devices for being disposed about other limbs of the wearer's body, are within the scope of this invention, such as a wrap around a patient's chest in the treatment of breast cancer.

A numerical study performed by R. D. Kamm, titled "Bioengineering Studies of periodic External Compression as Prophylaxis Against Deep Vein Thrombosis—Part I: Numerical Studies" concluded, among other things, that "the entire length of the veins should be emptied as full and as rapidly as possible." The Kamm study reviews three types of compression, the one of interest is wavelike compression. Wavelike compression is most similar to sequential compression provided by the illustrated embodiments of the present invention. The Kamm Study found wavelike compression is most effective in moving blood for an effective prophylaxis treatment.

Referring to FIG. 1, the compression sleeve 10 comprises four layers secured together in the illustrated embodiment of the present invention. The scope of the present invention is not limited to four layers. More specifically, the compression sleeve comprises an inner layer, generally indicated at 12, on which a first intermediate layer (broadly, a first bladder layer), generally indicated at 14, is overlaid. A second intermediate layer (broadly, a second bladder layer), generally indicated at 16, overlies the first intermediate layer 14 and is secured thereto. An outer cover generally indicated at 18, overlies and is secured to the second intermediate layer 16. In use, the inner layer 12 is disposed most adjacent to the limb of the wearer and is in contact with the limb of the wearer, and the outer cover 18 is most distant from the limb of the wearer. A knee opening 19 is formed through the sleeve 10 that is generally aligned with the back of the knee when the sleeve is applied to the leg. The layers have the same geometric shape and are superposed on each other so that edges of the layers generally coincide. It is contemplated that one or more of the layers 12, 14, 16, or 18 may not be superposed on a corresponding layer, but slightly offset to accommodate a particular feature of a patient's limb. Moreover, the number of sheets or thickness making up each layer 12, 14, 16, or 18 of the compression sleeve 10 may be other than described. The thickness of the layers may vary to add strength or to cause more expansion in one direction, such toward the limb, during inflation.

Figure 4:
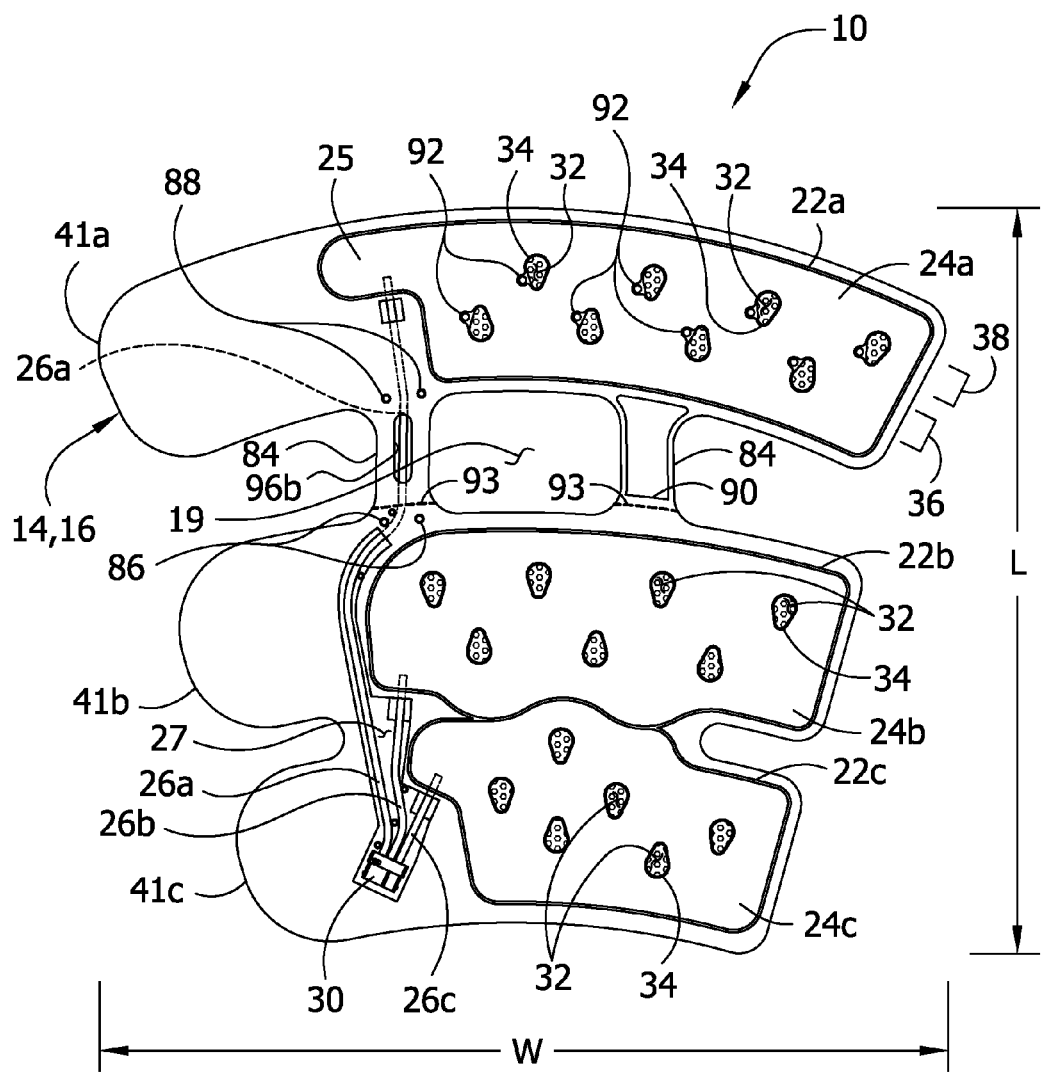
FIG. 4 is a front elevation of the compression sleeve with the outer cover removed.

Referring to FIGS. 1, 2 and 4, the first and second intermediate layers 14, 16, respectively, each include a single sheet of elastic material (broadly, "bladder material"). For example, the sheets 14 and 16 are made of a pliable PVC material as the bladder material. Layers 12 and 18 are made of a polyester material. The second intermediate layer 16 is secured to the first intermediate layer 14 via three separate bladder seam lines 22a, 22b, 22c defining a proximal bladder 24a, an intermediate bladder 24b and a distal bladder 24c, respectively, that are spaced apart longitudinally along the sleeve 10. The number of bladders may be other than three without departing from the scope of the present invention. As used herein, the terms "proximal", "distal", and "intermediate" represent relative locations of components, parts and the like of the compression sleeve when the sleeve is secured to the wearer's limb. As such, a "proximal" component or the like is disposed most adjacent to a point of attachment of the wearer's limb to the wearer's torso, a "distal" component is disposed most distant from the point of attachment, and an "intermediate" component is disposed generally anywhere between the proximal and distal components.

For reasons discussed below, the proximal bladder 24a defines a proximal, lateral extension 25 near the upper edge margin of the sleeve 10. The bladders 24a, 24b, 24c are circumferential bladders meaning that they are sized and shaped to be wrapped around substantially the entire circumference of the wearer's limb or very nearly the entire circumference of the limb. For example, in one embodiment the bladders 24a, 24b, 24c each extend around at least 90% of a median circumference of a leg. However, prior art devices have partial bladders such as AirCast® and HillRom®, and these prior art devices do not provide for openings, elasticity and other features of the present invention. It is to be understood that the construction described herein can be adopted by the prior art sleeves with a partial bladder construction, without departing from the scope of the present invention.

The intermediate layers 14, 16 may be secured together by radiofrequency welding, adhesive, or other chemical and/or mechanical process. It is understood that the intermediate layers 14, 16 may be secured together at other locations, such as around their peripheries and at bladder seam lines 22a, 22b, 22c to further define the shape of the inflatable bladders 24a, 24b, 24c. For purposes discussed below, the first intermediate layer 14 is secured to the inner layer 12 along a seam line 25 (FIGS. 5 and 6) that runs along the outer periphery of the first intermediate layer 14 so that central regions of the bladders 24a, 24b, 24c are not secured to the inner layer 12. This permits the bladders 24a, 24b, 24c to move relative to the inner layer 12. The second intermediate layer 16 may also be secured to the inner layer 12 along the same seam line 25. The first intermediate layer 14 may be secured to the inner layer 12 by RF welding or adhesive or in other suitable ways. This structure improves comfort as described below.

Referring to FIGS. 2 and 4, each inflatable bladder 24a, 24b, 24c receives fluid from a source of compressed fluid (not shown) via a dedicated proximal bladder tube 26a, intermediate bladder tube 26b, and distal bladder tube 26c, respectively, (FIG. 2). A tube line need not be dedicated to a bladder to practice the invention. Each tube 26a, 26b, 26c is disposed between the intermediate layers 14, 16 and secured to the respective bladder 24a, 24b, 24c by the respective bladder seam line 22a, 22b, 22c. As shown best in FIGS. 2 and 4, the first intermediate layer 16 defines a cutout 27 (FIG. 2) so that portions of the tubes 26a, 26b, 26c are not disposed between the intermediate layers. Other ways of securing the tubes 26a, 26b, and 26c to the bladders 24a, 24b, and 24c are within the scope of the invention. The opposite ends of the tubes 26a, 26b, 26c are grouped together using a second connector 30 (FIGS. 1 and 2) that is adapted to fluidly connect the tubes to the source of compressed fluid. The source of compressed fluid may be an air compressor under the control of a microprocessor that sequentially pressurizes the bladders as is generally known in the art. An exemplary air compressor is described in U.S. Pat. No. 5,876,359 to Bock, the disclosure of which is incorporated herein by reference. The bladders 24a, 24b, 24c may be configured to contain air pressurized to at least about 10 mm Hg (1333 Pa) to about 45 mm Hg (6000 Pa). The bladders should be capable of being repeatedly pressurized without failure. Materials suitable for the sheets include, but are not limited to, flexible PVC material that will not stretch substantially. In another embodiment, the intermediate layers may form a chamber for receiving an inflatable bladder that is formed separate from the chamber. In this embodiment, the layers may not be capable of containing pressurized air as along as the inflatable bladders are so capable. It will be noted that the bladders 24a, 24b, 24c can have openings 32 extending completely through the bladders, as described in the embodiments of the present invention.

Referring particularly to FIGS. 1 and 4, the sleeve 10 defines a connecting section including a pair of bridge members 84 on opposite sides of the knee opening 19 that extend between and connect a proximal portion of the sleeve that includes the proximal bladder 24a to the remainder of the sleeve. The proximal tube 26a generally lies along an axis of bridge member 84 to provide structural, lengthwise support to the sleeve 10. As shown best in FIG. 4, the cutout 27 in the intermediate sheet 16 does not extend through the bridge member 84. The proximal tube 26a extends between spaced apart distal spot welds 86 disposed adjacent to a distal end of the bridge member 84 and between spaced apart proximal spot welds 88 disposed adjacent to a proximal end of the bridge member. The spot welds secure the tube 26a to the bridge member 84 such that the proximal bladder tube 26a constitutes a rigid structural component (broadly, a "first rigid structural component") for maintaining the spacing between the proximal bladder 24a and the intermediate bladder 24b and in maintaining the longitudinally structural integrity of the connecting section. In other words, the sleeve 10 is rigidified against collapsing or sliding down the wearer's leg. As explained above, the proximal bladder tube 26a is secured to the proximal bladder 24a at the proximal, lateral extension 25. The proximal bladder tube 26a runs along a side of a distal portion of the proximal bladder 24a so that it does not enter the bladder until it reaches the proximal, lateral extension 25. Being secured at the proximal, lateral extension 25 of the bladder 24a provides additional longitudinal support to the sleeve 10 because the proximal bladder tube 26a extends lengthwise across more of the proximal portion of the sleeve than if the tube was secured at a distal portion of the bladder. In one embodiment, the proximal bladder tube 26a extends at least a quarter of the way across a thigh section of the sleeve 10. In another embodiment shown in FIG. 4, the tube 26a extends more than half way across the thigh section. This helps to keep the proximal portion of the sleeve 10 from collapsing and/or sliding out of position down the wearer's leg.

Referring to FIGS. 2 and 4, in addition to the proximal bladder tube 26a, a second rigid structural component 90, disposed between the intermediate layers 14, 16 and extending within the other bridge member 84 of the connecting section, also provides longitudinal structural support to the sleeve 10. The second structural component 90 extends between proximal and distal ends of the bridge member 84. The respective proximal and distal ends of the structural component 90 are wider than an intermediate portion of the component and the periphery of the component generally conforms to the peripheries of side walls of the bridge member 84 so that the structural component is secured to the bridge member.

Figure 3:
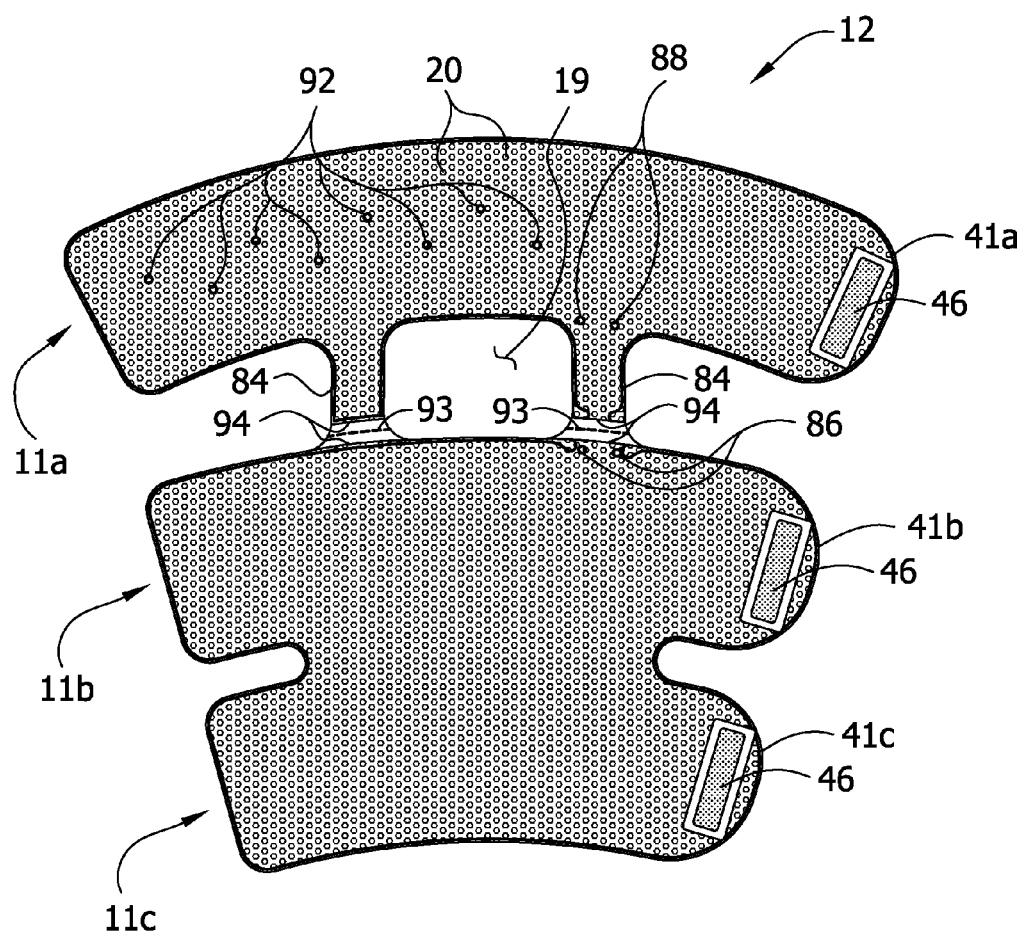
FIG. 3 is a rear elevation of an inner layer of the compression sleeve.

Referring to FIGS. 1, 3 and 4, the proximal bladder 24a is secured to the inner layer 12 and the outer cover 18 at spot welds 92 adjacent to the bladder openings 32 and within an outer perimeter of the bladder defined by the bladder seamline 22a. The spot welds 92 maintain the outer cover 18 and the inner layer 12 in proper position with respect to the bladders 24a, 24b, 24c. In other words, the spot welds 92 prevent the bladders 24a, 24b, 24c from substantially shifting relative to the inner layer 12 and the outer cover 18 while still providing the sleeve 10 with substantial flexibility. Too much movement of inner layer 12 and the outer cover 18 with respect to the bladders 24a, 24b, 24c may reduce the fit of the sleeve, thereby leading to reduced efficacy of the compression therapy. The proximal bladder 24a is free from securement to the inner layer 12 and outer cover 18 other than at the spot welds 92 to maintain flexibility of the sleeve so that mobility of the patient's leg is not compromised. Inner layer 12 may be joined to layer 16 at the spot welds 86, 88, 92 or the inner layer 12 may be joined at the seam line 34 of the opening 32. Away from the openings 32 and spot welds 86, 88, 92, the inner layer 12 is not joined to surface of the bladder material forming the bladder that expands to provide compression treatment to the patient's limb.

Figure 2B:
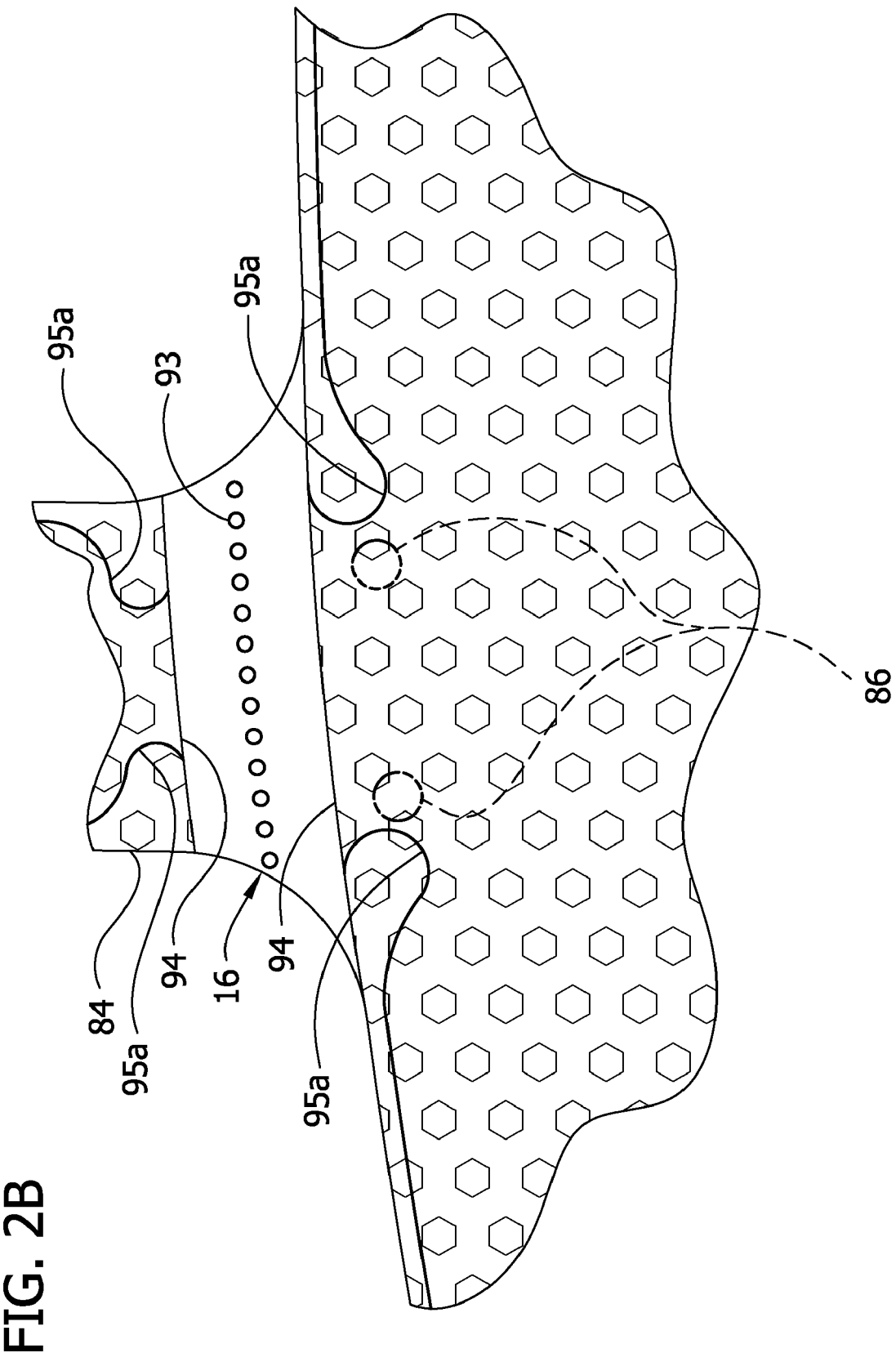
FIG. 2B is similar to FIG. 2A with the perforation line comprising circular openings.

In the illustrated embodiment, the thigh section 11a is removable from the remainder of the sleeve 10. In particular, the proximal portion of the sleeve 10 that includes the proximal bladder 24a and the bridge members 84 are removable from the remainder of the sleeve. Tear lines (broadly, lines of weakness) comprising perforation lines 93 in the intermediate layers 14, 16, extend transversely across the intermediate layers adjacent to where the bridge members 84 join thigh section 11a to the knee and ankle sections 11b, 11c. In a preferred embodiment, the removal is destructive and permanent. It is understood that the sleeve may include one tear line or more than two tear lines within the scope of the invention. It is also understood that the shapes of the perforations may be circular (FIG. 2B) or slot-shaped (FIG. 2C) or other shapes within the scope of the invention. Other ways of weakening the sleeve 10 at the tear lines besides the perforation lines 93 are within the scope of the present invention. For example, the tear lines may include a thinned out portion of the intermediate layers 14, 16. It is also understood that the tear lines may be used in other types of compression devices other than the illustrated compression sleeve. For example, a compression device with two bladders and a compression device with more than three bladders are within the scope of the invention. Still further, the tear lines may be positioned to disconnect different ones of the sleeve sections (i.e., besides the thigh section 11a).

Figure 2D:
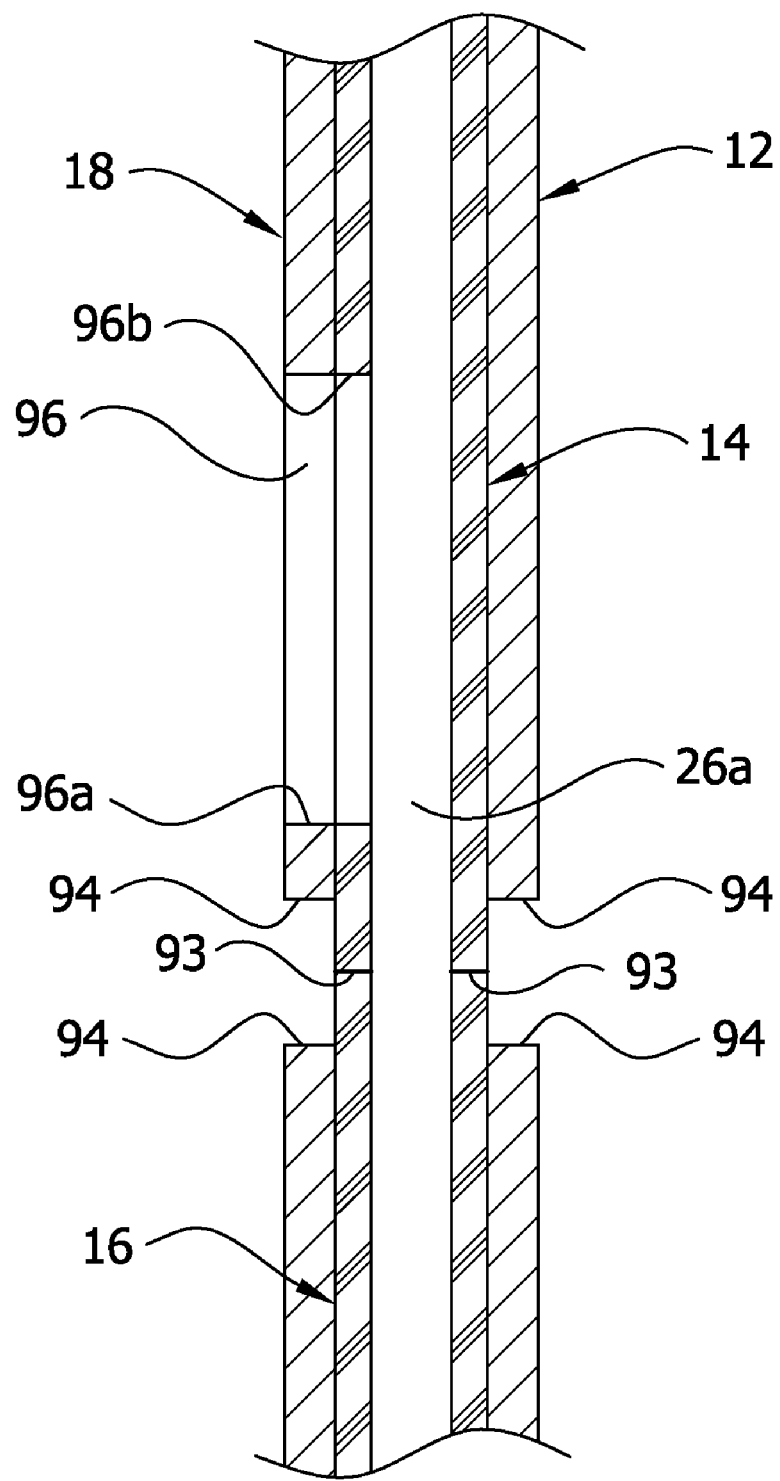
FIG. 2D is a section taken in the plane including line 2D-2D in FIG. 2A.
Figure 2E:
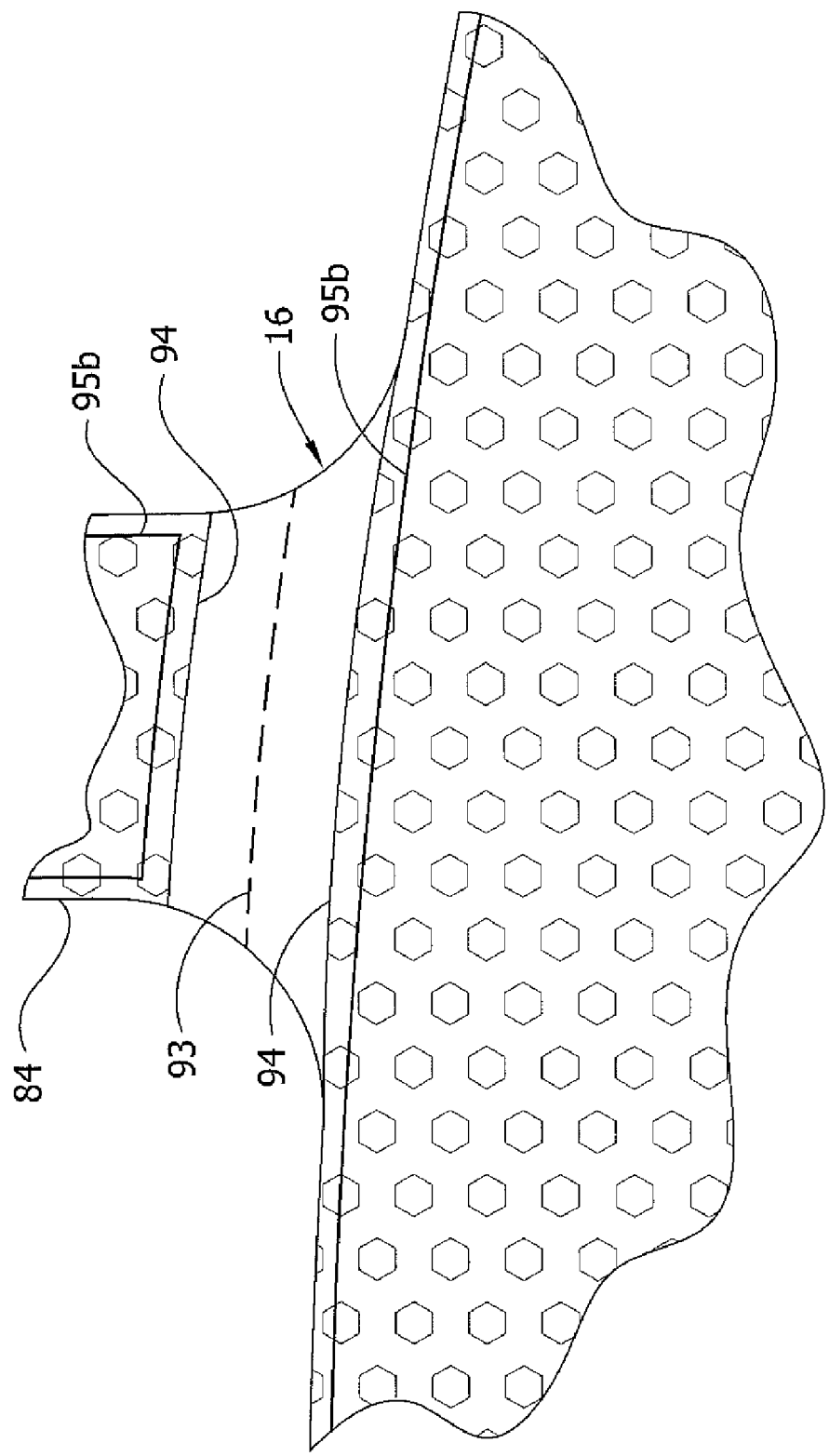
FIG. 2E is an enlarged, fragmentary view of FIG. 1 showing a perforation line extending across a right bridge of the compression sleeve.

Neither the inner liner 12 nor the outer cover 18 have lines or weakness, although such a configuration is contemplated and within the scope of the present invention. Instead, as shown best in FIGS. 2A and 2D, both the inner liner 12 and the outer cover 18 are discontinuous generally adjacent to the perforation lines 93 in the intermediate layers 14, 16 so as to define respective opposing terminal edge margins 94 adjacent to the perforation lines. Each perforation line 93 is disposed between respective opposing terminal edge margins 94 of the inner liner 12 and the outer cover 18. In the illustrated embodiment, the terminal edge margins 94 of the inner liner 12 and the outer cover 18 are at least partially welded or otherwise secured to respective intermediate layers 14, 16 along terminal securement lines 95a, 95b associated with the respective left and right bridge members 84. The weld lines 95a, 95b are contiguous with the seamline 42 securing the bladder layers 14, 16 to the inner liner 12 and outer cover 18. Each of the terminal securement lines 95b associated with the right bridge member 84 (FIG. 2E) are continuous and extend across the bridge member. However, the terminal securement lines 95a that are associated with left bridge member 84 (FIGS. 2A-2C) are discontinuous and do not extend across the proximal bladder tube 26a. Instead, the terminal securement lines 95a extend part way toward the center of the bridge 84, but turn back and curve down to the end of the terminal edge margins 94. The securement lines 95a thus form opposed inwardly projecting portions on opposite sides of the bladder tube 26a and facilitate location of the bladder tube. However, the weld lines 95a do not permanently join the bladder tube 26a so that it can be removed, as described hereinafter.

Generally, each terminal edge margin 94 is connected to the intermediate layers 14, 16 on a respective opposite side of the perforation line 93. By making the inner liner 12 and the outer cover 18 discontinuous at locations adjacent to the perforation lines 93 in the intermediate layers 14, 16, the sleeve is more easily torn at the perforation lines than if the inner liner and the outer cover were continuous and included perforation lines like the perforation lines in the intermediate layers. Moreover, the sleeve's resistance to tearing is greater at the terminal securement lines 95a, 95b. This greater tear resistance at the terminal securement lines 95a, 95b facilitates more precise tearing of the sleeve along the perforation lines 93 and prevents incidental, significant deviation from the tear lines. It is understood that the tear lines may be in other locations other than illustrated for removing the thigh section 11a from the remainder of the sleeve 10. As illustrated, the knee and ankle sections 11b, 11c do not have tear lines between them. It is also understood that the sleeve 10 may be configured to have other removable portions in addition to or instead of the thigh section 11a within the scope of the present invention.

As described previously, the proximal bladder tube 26a is disposed between the intermediate layers 14, 16 and extends through one of the bridge members 84. The proximal bladder tube 26a is releasably secured to the connector 30 so that the proximal bladder tube can be disconnected from the connector and so that the thigh section 11a can be removed from the remainder of the sleeve 10. The connector 30 and the proximal bladder tube 26a may be of the type disclosed in pending U.S. patent application Ser. No. 10/784,607, filed Feb. 23, 2004 and assigned to the assignee of the present application, the entirety of which is herein incorporated by reference. In particular, the connector 30 permits non-destructive disconnection of the proximal bladder tube 26a in preparation for removing the thigh section 11a. Because the proximal bladder tube 26a extends through one of the bridge members 84 generally transverse to the tear line, it may be difficult to tear the sleeve 10 along the corresponding perforation lines in the intermediate layers 14, 16. Accordingly, a tube access opening or window 96 is formed by an opening 96a in the outer cover 18 and an aligned opening 96b in the second intermediate layer 16. Because the window extends through the outer cover 18 and the second intermediate layer 16 adjacent to the outer cover to expose a portion of the proximal bladder tube to facilitate removal of the proximal bladder tube 26a from the bridge member 84 before tearing the sleeve 10. In the illustrated embodiment, the tube access window 96 is generally oblong and extends less than the full axial length of the bridge member 84. In use, the proximal bladder tube 26a can be disconnected from the connector 30 and then pulled through the tube access window 96 so that the tube no longer extends past the tear line between the intermediate layers 14, 16. With the tube 26a removed from between the intermediate layers 14, 16 at the corresponding tear line, the sleeve can be easily torn along the perforation lines 93 to remove the proximal portion, including the proximal bladder 24a, and the bridge members 84.

In one embodiment, the bladders 24a, 24b, 24c are constructed to expand more toward the wearer than away from the wearer, thereby applying a greater compressive force on the wearer's limb. In one example, the first intermediate layer 14 (i.e., the layer most adjacent to the inner layer 12) has a lesser thickness than that of the second intermediate layer 16. With both layers 14, 16 being of the same material (i.e., elastic PVC material) the first intermediate sheet will have a lower modulus of elasticity. Thus, when air is introduced into the bladders 24a, 24b, 24c, the bladders will expand more toward the inner layer 12 and the wearer than away from the wearer. It is understood that other ways, besides a difference in thickness between the intermediate layers 14, 16, of constructing the bladders 24a, 24b, 24c so that they expand more toward the wearer than away from the wearer is within the scope of the invention.

Referring to FIGS. 2 and 3, the inner layer 12 is constructed of a material that is capable of wicking moisture near a patient's limb. It is understood that the inner liner 12 may be of other configurations, may have other characteristics and properties, and may be formed from other material than described below. The inner (or "wicking") layer 12, through capillary action, absorbs moisture trapped near the leg or limb of the wearer, carries the moisture away from the surface of the limb, and transports the moisture from locations on the limb at the inner layer 12 where the moisture is abundant to areas where it is less abundant, at the openings 32, for evaporation to the ambient environment. The openings may be of various sizes, shapes and locations within the bladder area providing the compression. An opening 32 exposes the wicking layer to the ambient or surrounding air as opposed to the portion of the wicking layer beneath the bladder material. The portions of the inner layer 12 in registration with the openings 32 may be referred to as "exposed portions". Other ways of exposing the wicking material are within the scope of this invention, such as slits or extending the wicking material outside the perimeter of the bladder material. The present invention has its exposed portion within the bladder area that provides compression. The compression region is the bladder area expanding and contracting under the influence of air pressure or other fluids. The area of the bladder not providing compression is the seamline or weld points which are points of the bladder material sealed together to provide an air or water tight boundary or other regions of the opposed sheets 14, 16 outside the perimeter of the bladder. The wicking material 12 may be inter-weaved with the impervious material to form the inner layer 12. The wicking material 12 transports moisture to an area of less moisture. The openings 32 must be engineered to maintain blood velocity, while maximizing evaporation of moisture. Suitable wicking materials may be comprised of, for example, some form of, polyester, although they may be comprised of polypropylene. Microfibers may be used. Suitable microfiber materials include, but are not limited to, CoolDry model number CD9604, sold by Quanzhou Fulian Warp Knitting Industrial Co., Ltd., Quanzhou City, Fujian Province, China and Cool-Max®, sold by E. I. du Pont de Nemours and Company, Wilmington, Del.

The construction of wicking layer, openings, bladder and outer layer is discussed. The openings must be sized and shaped to maintain the blood flow efficacy of a compression sleeve like model 9529 and to provide improved evaporation of moisture for increasing patient compliance. For example and without being limiting, Table 1 (below) illustrates exemplary percentages and open areas of the openings 32 in each of small knee-length compression sleeves, medium knee-length compression sleeves, medium thigh-length compression sleeves, and large thigh-length compression sleeves. Other percentages and open areas are within the scope of the invention.

TABLE 1

| | Small Knee | Medium Knee | Medium Thigh | Large Thigh |
|---|---|---|---|---|
| % open area of bladders* | 1.64% | 5.97% | 9.44% | 7.50% |
| % open area of entire sleeve | 0.94% | 3.93% | 4.44% | 3.35% |
| open area of one aperture in²** | 0.247 | 0.61 | 0.68-0.88 | 0.67-0.86 |

*all three bladders combined.
**thigh length sleeves have larger apertures in the thigh bladder, therefore a range of sizes is provided.

Referring to FIGS. 1 and 4, the sleeve 10 is constructed so that portions of the intermediate layers 14, 16 do not overlie the inner layer 12 so that moisture wicked by the inner layer 12 travels to open portions of the inner layer 12 and evaporates to the atmosphere. In this illustrated embodiment, each inflatable bladder 24a, 24b, 24c includes openings 32 that extend through the first and second intermediate layers 14, 16, respectively, to the inner layer 12. One way to form such an opening is to seal the intermediate layers 14, 16 together within the periphery of the respective bladder 24a, 24b, 24c using a continuous sealing line 34. The portions of the intermediate layers 14, 16 within a periphery of the sealing line 34 can be removed, such as by cutting, thereby forming the openings 32. Other ways of forming the openings 32 are within the scope of this invention. Once an opening size and pattern is determined, a metal die is cast to cut the openings in the PVC bladder material for the opposing sheets.

For the preferred embodiment, the opening shape is generally shaped like a waterdrop. Each opening 32 is tapered from a first round end portion toward a second, smaller round end portion. The openings 32 may be of other shapes, such as circles, ovals, and slits, without departing from the scope of the invention. The opening shapes may be inter-mixed at the bladder without departing from the scope of the invention With respect to each bladder 24a, 24b, 24c, the openings 32 are arranged in a distal row 36 and a proximal row 38 (FIG. 4). Both rows 36, 38 extend across the respective bladder 24a, 24b, 24c along the width W of the sleeve 10. As depicted in the drawings, the openings 32 in each proximal row 38 are inverted medium waterdrop-shaped openings in that the openings taper distally, while the openings in each distal row 36 are right-side-up in that the openings taper proximally. The openings 32 in each distal row 36 are offset along the width W of the sleeve from the openings in the respective proximal row 38. Offsetting the openings 32 distributes the openings evenly across the surface area of the bladders 24a, 24b, 24c, thereby increasing the breathability of the bladders and the overall breathability of the sleeve 10 without compromising the structural integrity of the bladders or their ability to apply compressive force (i.e., prophylaxis treatment) to the leg or body part. Moreover, offsetting the openings in the respective distal and proximal rows 36, 38, also makes the bladders 34a, 34b, 34c more stretchable in the widthwise direction of the sleeve 10. Other ways of allowing fluid wicked by the inner layer 12 to evaporate, besides the openings 32 through the bladders are within the scope of the invention.

Referring to FIGS. 1 and 2, the outer cover 18 of the compression sleeve 10 is constructed of a single sheet of material. The outer cover 18 is breathable and has a multiplicity of openings 40 or perforations so that it has a mesh construction to provide even more breathability. It is understood that the outer cover 18 may be of other configurations, may have other characteristics and properties, and may be formed from other material than described below. A suitable material for the outer cover 18 may be a polyester mesh. The rate of evaporation from the openings is improved by treating the fibers of the mesh material with a hydrophilic material. The mesh material will absorb the wicked fluid more readily. Wicking fibers of this type are indicated generally at 21 in FIG. 7. These hydrophilic fibers lower the surface tension of the mesh material to allow bodily fluids to more easily absorb into the fibers and spread therethrough for a more efficient evaporation of the wicked fluid. Absorbing fluid more readily will allow the fluid to move to the open areas more quickly for evaporation. The capillary effect is made more efficient as the absorbed fluid at the openings is moved more quickly through the mesh outer cover 18.

Figure 5:
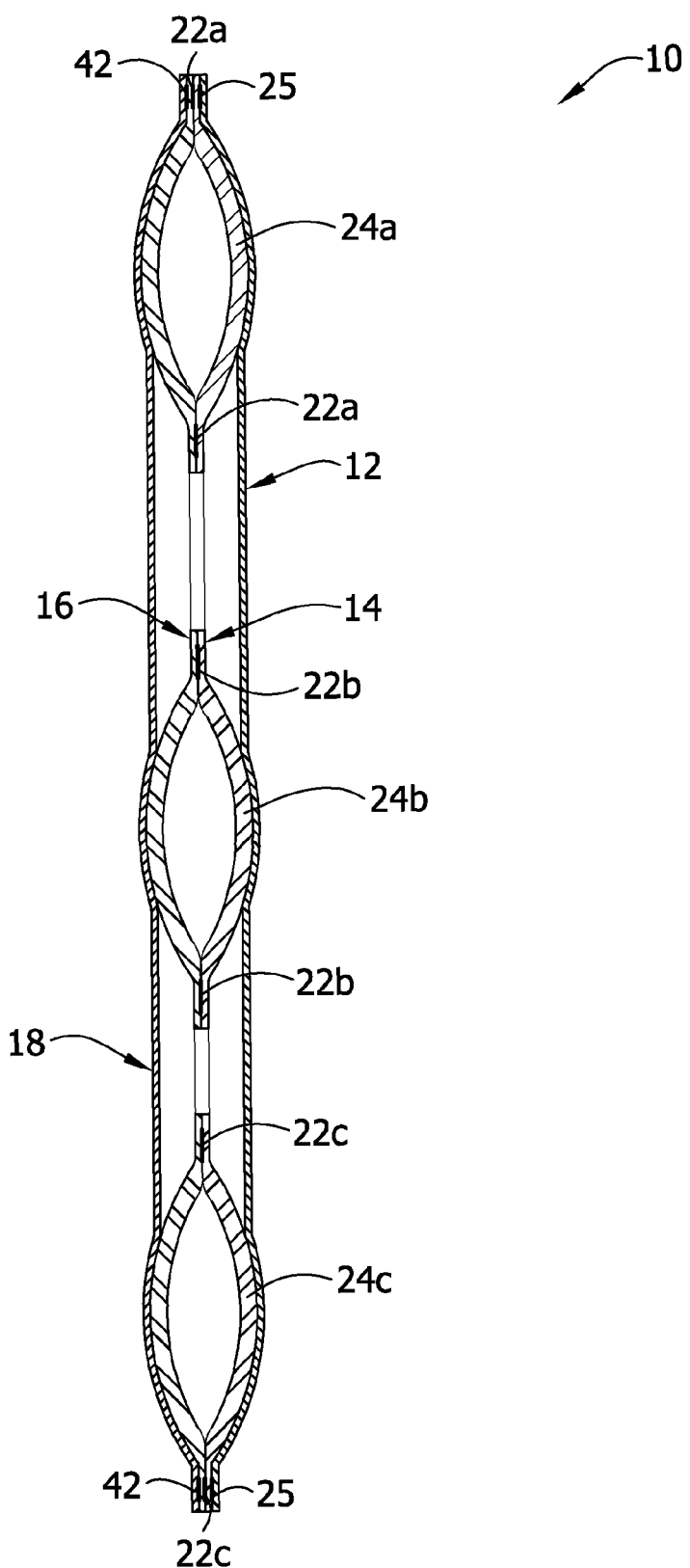
FIG. 5 is a longitudinal section of the compression sleeve with inflatable bladders of the sleeve in an inflated state.
Figure 6:
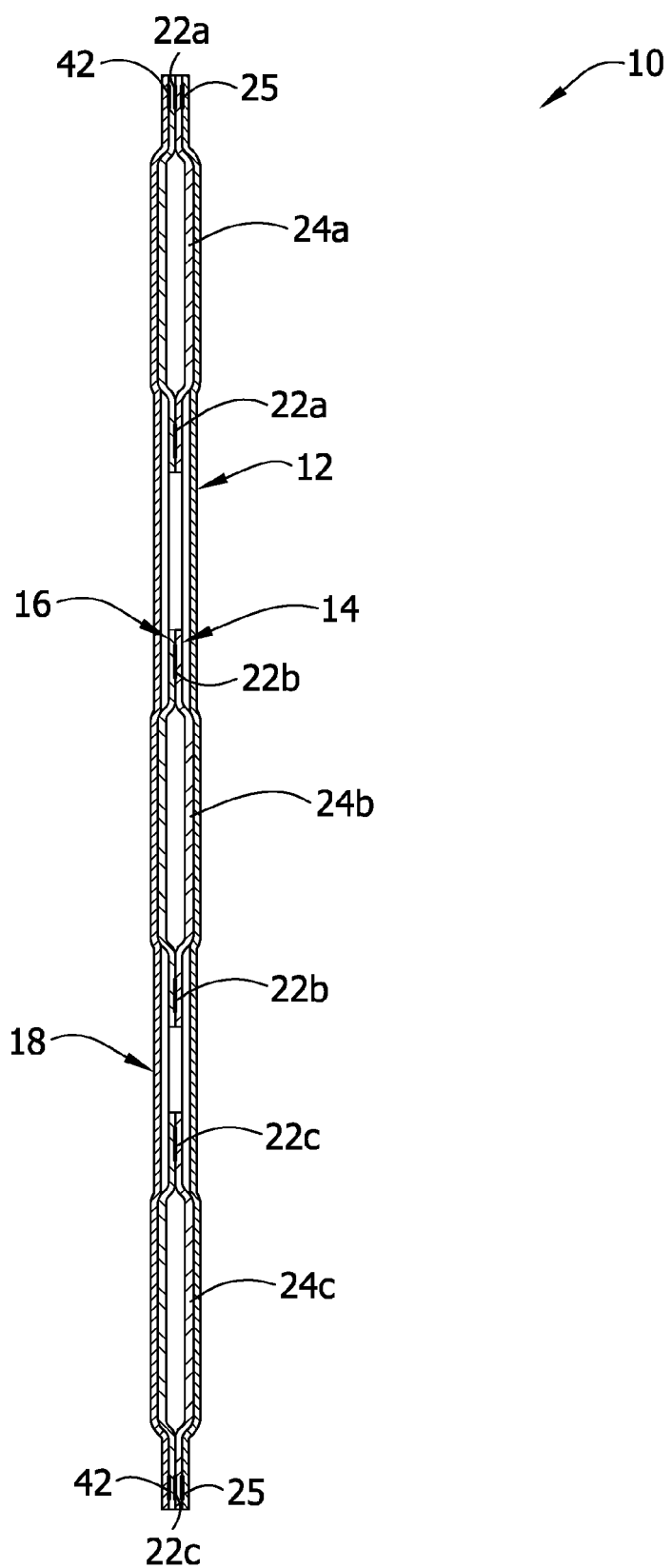
FIG. 6 is a longitudinal section of the compression sleeve with the inflatable bladder in a deflated state.

Referring to FIGS. 1, 5 and 6, the outer cover 18 is secured to the second intermediate layer 16 along seam line 42, which runs only adjacent to the outer periphery of the second intermediate layer so that the bladders 24a, 24b, 24c are free from attachment to the cover. The second intermediate layer 16 may be secured to the inner layer 12 by RF welding or adhesive or in other suitable ways.

Figure 7:
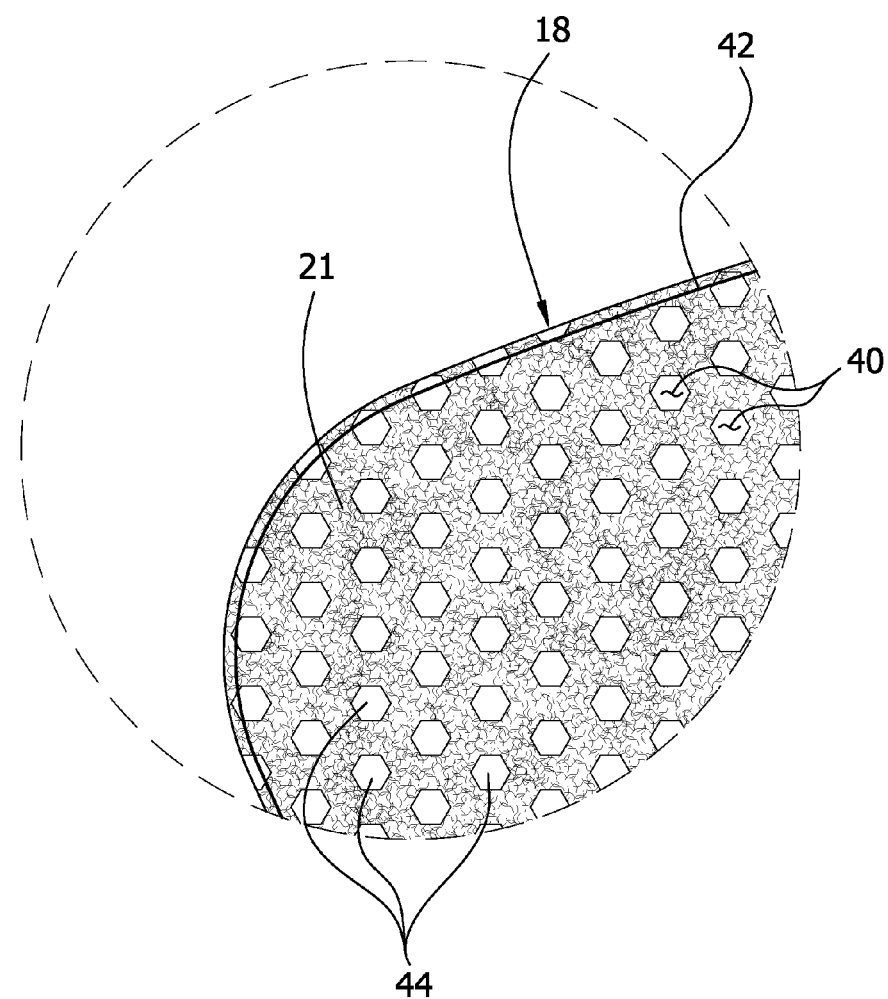
FIG. 7 is an enlarged fragmentary elevation of the outer cover illustrating loop material.

Referring to FIGS. 1 and 7, the entirety of an outer surface of the outer cover 18 also acts as a fastening component of a fastening system for securing the sleeve 10 to the limb of the wearer. In a particular embodiment, the outer cover 18 of mesh (FIG. 7), for example, has an outer surface comprising loops 44 (FIG. 7) that acts as a loop component of a hook-and-loop fastening system. A mesh construction, as shown in FIG. 7, has interconnected or weaved fibers 21 of material forming the outer cover 18. The loops 44 may be formed as part of the material of the outer cover 18 or otherwise disposed on the surface of the outer cover. A suitable material with such construction is a polyester mesh loop 2103 sold by Quanzhou Fulian Warp Knitting Industrial Co., Ltd. of Quanzhou City, China. Hook components 46 (FIG. 3) are attached to an inner surface of the inner layer 12 at the proximal, intermediate and distal flaps 41a, 41b, 41c, respectively. The loops 44 of the outer cover 18 allow the hook components 46 (FIG. 3) to be secured anywhere along the outer surface of the outer cover when the sleeve 10 is wrapped circumferentially around the limb of the wearer. This allows for sleeve 10 to be of a substantially one-size-fits-all configuration with respect to the circumferences of different wearers' limbs. Moreover, the outer cover 18 having the loops 44 allows the practitioner to quickly and confidently secure the sleeve 10 to the wearer's limb without needing to align the fastening components.

It is contemplated that the outer cover 18 may be capable of wicking fluid in addition to being breathable. For example, the outer cover 18 may be constructed of the same material as the inner layer 12 (e.g., Cool dry). In this way, the moisture wicked by the inner layer 12 may be wicked by the outer cover 18 through the openings 32 in the bladders 24a, 24b, 24c. The moisture will then spread out evenly across the outer cover 18 and is able to evaporate more readily than if the outer cover was not formed of a wicking material because a greater surface area of the outer cover, as opposed to the inner layer 12, is exposed to air. Alternatively, the cover can have a wicking material laced in or on top of outer layer.

The compression sleeve 10 as a whole is more comfortable to wear because of the synergistic relationship of the layers 12, 14, 16, 18. For example, the inner layer 12 is capable of wicking moisture from the limb and allowing the moisture to evaporate out of the sleeve 10. As stated above, wicking involves transporting moisture away from the limb and moving moisture from locations where it is abundant and transporting it to areas where it is less abundant. Material decreases its wicking rate when the moisture is equally distributed in the wicking material and the wicking material is saturated. However, the breathability of the sleeve 10 allows for the wicked moisture to evaporate. The waterdrop-shaped openings 32 in the bladders 24a, 24b, 24c and the breathable outer cover 18 allow moisture in the inner layer 12 that is adjacent to the openings to evaporate therethrough. Accordingly, as the moisture evaporates, it is transported to the drier portions of the inner layer 12, and the inner layer is able to wick more moisture.

To improve patient mobility, the sleeve was designed to have an elastic inner layer 12 and outer cover 18. An elastic sleeve improves comfort which increases patient compliance. Refer to FIGS. 1-7 for the discussion on elasticity below. An elastic device will conform to a patient's limb to ensure continuous wicking. A compliant or substantially conforming fit will help ensure the contact of the bladder against a patient's skin during use. The bladder applies the pressure to move the blood. The elastic outer layer helps reduce number of straps to hold the sleeve in place because the elastic outer layer 18 returns its original shape exerting a slight force against the patient's limb. This force helps hold the sleeve in place and also allows the practitioner not to over tighten a strap. Some prior art devices use an elastic stocking, such as the T.E.D.® stocking, beneath the compression sleeve. The compression sleeve of at least some embodiments avoids the two step process of first placing the compression stocking on the patient, then placing the sleeve over the stocking. Also sleeves of preferred embodiments of the present invention simplify the job of the nurses because there is no need to order a stocking and sleeve.

The Applicant devised an elasticity test for determining the amount of stretch around the limb and along the limb. A patient needs to be mobile during treatment. Prior art sleeves can be awkward, stiff and heavy so the user would remove the device, if they needed to move about. The need is to improve elasticity without distorting the openings 32 too much such as becoming elongated or causing an opening to overlie, which reduces its size for evaporation.

For example, the inner layer 12 is preferably elastically stretchable along the width W of the sleeve 10 so that the inner layer is able to conform circumferentially to the shape of the wearer's limb. Conforming circumferentially allows the inner layer 12 to remain in close, intimate and continuous contact with the wearer's limb to ensure that the inner layer is continuously wicking moisture from the limb. The inner layer 12 may also be stretchable the length L. Preferably, the inner layer 12 is elastically stretchable along both the width W and the length L of the sleeve and is more elastically stretchable along the length of the sleeve 10 than along the width. Summarizing the preferred approach, using the test described below, the inner layer 12 may have an average elasticity in the widthwise direction of the sleeve of between about 13 lbs/in (23 N/cm) and about 14 lbs/in (25 N/cm), and in one embodiment has an elasticity of about 13.3 lbs/in (23.3 N/cm). The inner layer 12 may have an average elasticity in the lengthwise direction of the sleeve of between about 0.5 lbs/in (0.9 N/cm) and about 0.7 lbs/in (1.2 N/cm), and in one embodiment has an elasticity of about 0.63 lbs/in (1.10 N/cm). The small openings 20 in the inner layer 12 also allow for the inner layer stretch more.

The outer cover 18 is also elastically stretchable along the length L of the sleeve 10 or stretchable along both lengthwise and widthwise (circumferentially). Preferably, the outer cover 18 is more elastic longitudinally than widthwise. Although elastically stretchable, the outer cover 18 acts to restrain the amount of expansion of the bladders 24a, 24b, 24c. The outer cover 18 helps to conform the bladder to the limb for helping to evenly apply pressure for moving blood. For example, using the elasticity test described below, the outer cover 18 may have an average elasticity in the widthwise direction of between about 13 lbs/in (23 N/cm) and about 15 lbs/in (26 N/cm), and in one embodiment has an elasticity of about 13.6 lbs/in (23.8 N/cm). The outer cover 18 may have an average elasticity in the longitudinally direction of between about 19 lbs/in (33 N/cm) and about 22 lbs/in (39 N/cm), and in one embodiment an elasticity of about 19.8 lbs/in (34.7 N/cm).

The compression sleeve 10 as a whole is stretchable longitudinally by way of the longitudinally stretchable inner layer 12, intermediate layers 14, 16 and outer cover 18. Further, the sleeve 10 is slightly stretchable widthwise by way of the abilities of the inner layer 12, intermediate layers 14, 16 and the cover 18 to stretch widthwise. The waterdrop-shaped openings 32 and the fact that the openings are offset widthwise also aid in the widthwise stretching.

It is common for patients that have undergone surgery to incur swelling of the limbs. The widthwise stretching of the sleeve 10 is more comfortable for patients that experience swelling because the sleeve will stretch, i.e., increase in size circumferentially, as the limb swells. Moreover, elasticity of the sleeve 10 allows the wearer to have more mobility of his or her limb and gives the practitioner a greater degree of freedom when wrapping the sleeve around a wearer's leg. For example, using the elasticity test described below, the thigh-length sleeve 10, comprising the inner layer 12, the intermediate layers 14, 16 and the outer cover 18 as described above, may have an average elasticity in the widthwise direction of between about 22 lbs/in (39 N/cm) and about 27 lbs/in (47 N/cm), and in one embodiment an elasticity of about 24.3 lbs/in (42.6 N/cm). The compression sleeve 10 may have an average elasticity in the lengthwise direction of between about 17 lbs/in (30 N/cm) and about 22 lbs/in (39 N/cm), and in one embodiment an elasticity of about 19.4 lbs/in (34.0 N/cm).

In another example, using the elasticity test described below, a knee-length sleeve, comprising an inner layer, intermediate layers and outer cover of the same material as the thigh-length sleeve described above, may have an average elasticity in the widthwise direction of between about 22 lbs/in (39 N/cm) and about 27 lbs/in (47 N/cm), and an average elasticity in the lengthwise direction of between about 33 lbs/in (58 N/cm) and about 40 lbs/in (70 N/cm).

The following test (herein referred to as the "elasticity test") is used to measure the elasticity of the layers 12, 14, 16 and 18 and the sleeve 10, both widthwise and lengthwise. First, structure clamps are secured to the structure (e.g., one of the layers 12, 14, 16, and 18 or the sleeve 10) to be tested. When testing the lengthwise elasticity, the structure clamps are secured to top and bottom edges of the structure. When testing the widthwise elasticity, the structure clamps are secured to opposite side edges of the structure. The sleeve sample with the structure clamps secured thereto is placed in a universal tensile testing machine (such as a universal testing machine manufactured by Instron® of Grove City, Pa.) by securing the structure clamps to opposing machine clamps of the machine. The machine should include a microprocessor having a tensile force measurement program used to control the machine and record measurements of force and displacement. Once the structure is secured in the machine, the opposing machine clamps are moved apart to a position that eliminates or minimizes the slack in the structure. This position is the initial position for all subsequent tests. The tensile force measurement program is then executed. The displacement of the sleeve sample as the machine clamps are moved apart should be uniform linear elongation and should not damage the structure. This displacement is set and maintained for each test repetition. The test is repeated 7 times for each layer 12, 14, 16 and 18 and the sleeve 10. Elasticity is calculated as force (lbs) divided by the displacement (in). An average elasticity of the 8 tests is calculated by summing the elasticity calculations for the 8 tests and dividing the sum by 8.

The sleeve in some embodiments is made more comfortable for the wearer by the fact that the inner layer 12 and the outer cover 18 are secured to the respective intermediate layers 14, 16 only adjacent to the outer peripheries of the inner layer and cover whereby the bladders 24a, 24b, 24c are not secure directly to the inner layer and cover. This construction allows for the bladders 24a, 24b, and 24c to move independently of the inner layer 12, and vice versa. Co-assigned U.S. patent application Ser. No. 11/299,568 disclosing an embodiment directed to reducing chafing of a person's skin during use is incorporated herein by reference.

Thus, when the sleeve 10 is wrapped circumferentially around the wearer's limb, the inner layer 12 substantially conforms to the contour or shape of the limb and will remain substantially stationary against the wearer's limb as the bladders 24a, 24b, 24c inflate and deflate and/or shift positions. The movement of the bladders 24a, 24b, 24c both as they inflate and deflate and shift positions relative to the limb may cause chafing and other discomfort for the patient if the surface of the bladders continuously rubbed against the limb. However, by being secured only at the outer peripheries of the intermediate layers 14, 16, the inner layer 12 creates a buffer between the bladders 24a, 24b, 24c and the limb that prevents chafing and other friction against the skin of the limb. The bladders 24a, 24b, 24c may move without causing corresponding movement of the inner layer 12 against the skin.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A device for applying compression treatment to a part of a wearer's body, the device comprising:

first and second opposing bladder layers secured to one another along two bladder lines to define first and second inflatable bladders spaced apart from one another along an axis of the device;

a connecting section including a portion of at least one of the first and second bladder layers extending between and connecting the first and second inflatable bladders to one another;

a line of weakness in the connecting section extending generally transverse to the axis of the device for selectively separating the inflatable bladders from one another;

an overlying layer in generally opposing relationship to one of the first and second bladder layers, the overlying layer being discontinuous generally adjacent to the line of weakness to define terminal edge margins of the overlying layer extending generally along the line of weakness, the terminal edge margins each being connected to at least one of the first and second bladder layers on an opposite side of the line of weakness from the other terminal edge margin.

2. A device as set forth in claim 1 wherein the terminal edge margins are spaced apart from each other on opposite sides of the line of weakness.

3. A device as set forth in claim 2 wherein the overlying layer includes separate first and second overlying layer portions spaced axially apart from each other along a line extending transverse to the axis of the device.

4. A device as set forth in claim 1 wherein the terminal edge margins of the overlying layer are secured to said one of the first and second bladder layers along the terminal edge margins.

5. A device as set forth in claim 4 further comprising a tube extending along the connecting portion for delivering air to the first inflatable bladder, wherein each terminal edge margin secured to said one of the first and second bladder layers along a discontinuous weld line that does not extend across the tube.

6. A device as set forth in claim 4 wherein the overlying layer is further secured to said one of the first and second bladder layers along perimeter securement lines running generally adjacent to a perimeter of the overlying layer, wherein at least a majority portion of the overlying layer within the perimeter of the overlying layer is free from securement to both the first and second bladder layers.

7. A device as set forth in claim 6 wherein the perimeter securement lines extend substantially continuously around the periphery of the overlaying layer.

8. A device as set forth in claim 1 wherein the overlying layer comprises a breathable mesh fabric material.

9. A device as set forth in claim 1 wherein the overlying layer comprises an inner liner in generally opposing relationship to the first bladder layer.

10. A device as set forth in claim 9 further comprising an outer cover in generally opposing relationship to the second bladder layer, the outer cover being discontinuous generally adjacent to the line of weakness to define terminal edge margins of the outer cover extending generally along the line of weakness, the terminal edge margins each being connected to the second bladder layer on an opposite side of the line of weakness from the other terminal edge margin.

11. A device as set forth in claim 9 further comprising a tube extending along the connecting portion for delivering air to the first inflatable bladder, wherein each terminal edge margin is connected to the second bladder layer along a discontinuous weld line that does not extend across the tube.

12. A device as set forth in claim 10 wherein the terminal edge margins of the outer cover are spaced apart from each other on opposite sides of the line of weakness.

13. A device as set forth in claim 12 wherein the outer cover includes separate first and second overlying layer portions spaced axially apart from each other along a line extending transverse to the axis of the device.

14. A device as set forth in claim 12 wherein the terminal edge margins of the outer cover are secured to the second bladder layer along the terminal edge margins.

15. A device as set forth in claim 1 wherein the line of weakness comprises a perforation line.

16. A device as set forth in claim 15 wherein the connecting section comprises portions of both the first and second bladder layers, wherein the line of weakness comprises perforation lines formed in both the first and second bladder layers.

17. A device as set forth in claim 1 wherein the device includes a knee opening sized and shaped to receive a knee of the wearer, the connecting portion comprising first and second bridge members on opposite sides of the knee opening extending from a distal section of the device that includes the second bladder to a proximal section of the device that includes the first bladder, wherein the line of weakness comprises a first line of weakness generally adjacent to where the first bridge member meets the distal section and a second line of weakness generally adjacent to where the second bridge member meets the distal section.

18. A device as set forth in claim 16 further comprising:
  a first tube in fluid communication with the first bladder for delivering pressurized fluid to the first bladder and a second tube in fluid communication with the second bladder for delivering pressurized fluid to the second bladder, the first tube extending across the first line of weakness and through the first bridge member between the first and second bladder layers; and
  a tube access opening extending through the second bladder layer in the first bridge member, a portion of the first tube being accessible through the tube access opening for withdrawing the first tube through the opening.

19. A device as set forth in claim 16 wherein the overlying layer comprises an outer cover in generally opposing relationship to the second bladder layer, wherein the tube access opening extends through the outer cover.

20. A method of making a compression device comprising:
  securing first and second opposing bladder layers to one another along two bladder lines to define first and second inflatable bladders spaced apart from one another along an axis of the device and having a connecting section extending between and connecting the first and second inflatable bladders to one another;
  forming a line of weakness in the connecting section extending generally transverse to the axis of the device for selectively separating the inflatable bladders from one another;
  securing an overlying layer in generally opposing relationship to one of the first and second bladder layers, the overlying layer being discontinuous generally adjacent to the line of weakness to define opposing terminal edge margins, wherein each of the terminal edge margins is secured to one of the first and second bladder layers on a respective opposite side of the line of weakness.

21. A method as set forth in claim 20 wherein said securing an overlying layer comprises securing the terminal edge margins of the overlying layer to said one of the first and second bladder layers at the terminal edge margins along the line of weakness, and securing the overlying layer to said one of the first and second bladder layers along a perimeter of the overlying layer, wherein at least a majority portion of the overlying layer within the perimeter of the overlying layer is free from securement to said one of the first and second bladder layers.

22. A method as set forth in claim 21 wherein said securing an overlying layer comprises securing an inner liner in generally opposing relationship to the first bladder layer, wherein the method further comprises securing an outer cover in generally opposing relationship to the second bladder layer, the outer cover being discontinuous generally adjacent to the line of weakness to define opposing terminal edge margins of the outer cover, wherein each of the terminal edge margins of the outer cover is secured to the second bladder layer on a respective opposite side of the line of weakness.

* * * * *